United States Patent
Vare et al.

(10) Patent No.: US 11,617,741 B1
(45) Date of Patent: Apr. 4, 2023

(54) METHOD FOR INHIBITING GROWTH OF BACTERIA

(71) Applicants: Health Research, Inc., Menands, NY (US); The Research Foundation for the State University of New York, Albany, NY (US); Duke University, Durham, NC (US)

(72) Inventors: Ville Vare, Albany, NY (US); Kathleen McDonough, Menands, NY (US); Ryan Schneider, Albany, NY (US); Paul Agris, Durham, NC (US); Thorsten Seyler, Durham, NC (US)

(73) Assignees: HEALTH RESEARCH, INC., Menands, NY (US); THE RESEARCH FOUNDATION FOR THE STATE UNIVERSITY OF NEW YORK, Albany, NY (US); DUKE UNIVERSITY, Durham, NC (US)

( * ) Notice: Subject to any disclaimer, the term of this patent is extended or adjusted under 35 U.S.C. 154(b) by 99 days.

(21) Appl. No.: 17/400,336

(22) Filed: Aug. 12, 2021

(51) Int. Cl.
| | |
|---|---|
| A61K 31/426 | (2006.01) |
| A01N 43/78 | (2006.01) |
| A61K 8/49 | (2006.01) |
| A61Q 17/00 | (2006.01) |
| A61K 31/7036 | (2006.01) |
| A01N 43/90 | (2006.01) |
| A01P 1/00 | (2006.01) |
| A61P 31/04 | (2006.01) |
| A61K 31/496 | (2006.01) |

(52) U.S. Cl.
CPC ............ *A61K 31/426* (2013.01); *A01N 43/78* (2013.01); *A01N 43/90* (2013.01); *A01P 1/00* (2021.08); *A61K 8/49* (2013.01); *A61K 8/494* (2013.01); *A61K 31/496* (2013.01); *A61K 31/7036* (2013.01); *A61P 31/04* (2018.01); *A61Q 17/005* (2013.01)

(58) Field of Classification Search
CPC .............................. A61K 31/426; A61P 31/04
See application file for complete search history.

(56) References Cited

U.S. PATENT DOCUMENTS

| | | |
|---|---|---|
| 6,706,869 B1 | 3/2004 | Wong et al. |
| 7,745,391 B2 | 6/2010 | Mintz et al. |
| 8,410,336 B2 | 4/2013 | Lutfiyya |
| 10,266,527 B2 | 4/2019 | Agris |
| 2004/0031072 A1 | 2/2004 | La Rosa et al. |
| 2004/0180380 A1 | 9/2004 | Lee et al. |
| 2005/0255491 A1 | 11/2005 | Lee et al. |
| 2013/0031668 A1 | 1/2013 | Brover et al. |

FOREIGN PATENT DOCUMENTS

| | | |
|---|---|---|
| JP | 2005097195 A | 4/2004 |
| WO | 2011057029 A1 | 5/2011 |
| WO | 2015061339 A1 | 4/2015 |

OTHER PUBLICATIONS

Ville Vare, slides presented during Junior Awards for Microbiology talk entitled "Development of novel small molecule antibiotics against Gram-positive bacteria" given in Albany, New York, Nov. 2018.
Spears, Jessica L. "Amino Acid Signature Enables Proteins to Recognize Modified tRNA," Biochemistry, vol. 53 No. 7, p. 1125-1133 (2014).
"Unnamed protein product [Trypanosoma congolense IL3000]; GenBank: CCD16211.1," GenBank (2012).
"Cobalt transporter [Bilophila wadsworthia]; NCBI Reference Sequence: WP 005029773.1," National Center for Biotechnology Information: Protein Database (2013).
"Hypothetical protein AMTR s00028p00129770 [Amborella trichopoda]; GenBank: ERN10592.1," GenBank (2013).
Hypothetical protein [Actinoplanes globisporus]; NCBI Reference Sequence: WP 020515231.1, National Center for Biotechnology Information: Protein Database (2013).
"Hypothetical protein [Caldilinea aerophila]; NCBI Reference Sequence: WP 014433126.1," National Center for Biotechnology Information: Protein Database (2012).
"Hypothetical protein [Segniliparus rugosus]; NCBI Reference Sequence: WP 021030245.1," National Center for Biotechnology Information: Protein Database (2013).
"Predicted: mucin-3A-like [Equus caballus]; NCBI Reference Sequence: XP 005613711.1," National Center for Biotechnology Information: Protein Database (2013).
"Hypothetical protein [Agrobacterium tumefaciens]; NCBI Reference Sequence: WP 0023501230.1," National Center tor Biotechnology Information: Protein Database (2013).
Frohlich, Kyla M. "Discovery of Small-Molecule Antibiotics against a Unique tRNA-Mediated Regulation of Transcription in Gram-Positive Bacteria," ChemMedChem, vol. 14, No. 7, p. 758-769 (2019).

(Continued)

*Primary Examiner* — Kamal A Saeed
(74) *Attorney, Agent, or Firm* — Heslin Rothenberg Farley & Mesiti P.C.

(57) ABSTRACT

Provided is a method for inhibiting the growth of Gram-positive bacteria, including contacting said bacteria with a first compound and a second compound, wherein the first compound is a compound of Formula I:

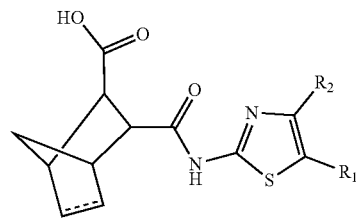

and the second compound is an antibiotic other than a compound of Formula I. Also provided is a composition including the first compound and the second compound.

23 Claims, 25 Drawing Sheets
(5 of 25 Drawing Sheet(s) Filed in Color)

(56) References Cited

OTHER PUBLICATIONS

Seyler, Thorsten M. "A New Promising Anti-Infective Agent Inhibits Biofilm Growth by Targeting Simultaneously a Conserved RNA Function That Controls Multiple Genes," Antibiotics, vol. 10, No. 41. p. 1-13 (2021).

Vare, Ville Y. P. "Small-Molecule Antibiotics Inhibiting tRNA-Regulated Gene Expression Is a Viable Strategy for Targeting Gram-Positive Bacteria," American Agents and Chemotherapy, vol. 65, No. 1 (2021).

Ville Vare, slides presented during Microbial Pathogenesis and Immunology talk entitled "Can we further improve the analogs?" given online from Albany, New York, Dec. 1, 2020.

Ville Vare, "Development of Small Molecule Antibiotics against a Conserved RNA Gene Regulatory Element in Gram-Positive Bacteria," Dissertation Submitted to the University at Albany, State University of New York in Partial Fulfillment of the Requirements for the Degree of Doctor of Philosophy, Dec. 22, 2020.

| Antibiotic class | Drug tested | Primary target | MIC alone (μg/ml) | MIC with PKZ18 analog (μg/ml) | PKZ18 analog used | Amt used (μg/ml) | Fold change | FIC | Effect |
|---|---|---|---|---|---|---|---|---|---|
| Aminoglycosides | Gentamicin | 16S rRNA (A-site) codon-anticodon reading | 0.50-1.00 | 0.031 | 18-22, 18-52, 18-53 | 8.000 | 8 | 0.38 | Synergistic |
| | Streptomycin | 16S rRNA (A-site) and S12 initial tRNA selection | 4.000 | 2.000 | 18-22 | 8.000 | 2 | 0.75 | Additive |
| | Hygromycin | 16S rRNA mRNA translocation | 64.000 | 32.000 | 18-22 | 8.000 | 2 | 0.75 | Additive |
| | Kanamycin | 16S rRNA and S12 wobble base pairing | 256.000 | 64.000 | 18-22 | 4.000 | 4 | 0.38 | Synergistic |
| | Neomycin | 16S rRNA (A-site) codon-anticodon reading | 256.000 | 32.000 | 18-22 | 8.000 | 8 | 0.38 | Synergistic |
| Beta-lactams | Ampicillin | Transpeptidase (cell wall) | 16-32 | 8.000-4.000 | 18-22, 18-53 | 16.000 | 4 | 0.75 | Additive |
| | Oxacillin | Transpeptidase (cell wall) | 0.500 | 0.500 | 18-22 | NA | 1 | 1.00 | Indifferent |
| Glycopeptides | Vancomycin | NAM/NAG-peptides (cell wall) | 0.500 | 0.500 | 18-22 | NA | 1 | 1.00 | Indifferent |
| Quinolones and fluoroquinolones | Ofloxacin | Topoisomerases and gyrase | 0.250 | 0.250 | 18-22 | NA | 1 | 1.00 | Indifferent |
| Tetracyclines | Tetracycline | Ribosomal A-site | 0.250 | 0.250 | 18-22 | NA | 1 | 1.00 | Indifferent |
| Other | Rifampin | RNA polymerase | 0.025 | 0.025 | 18-22 | NA | 1 | 1.00 | Indifferent |
| | Daptomycin | Membrane permeability (cell wall) | 4.000 | 4.000 | 18-22 | NA | 1 | 1.00 | Indifferent |
| | Mupirocin | IleRS | 0.125 | 0.125 | 18-22 | NA | 1 | 1.00 | Indifferent |
| | Chloramphenicol | 50S subunit (23S rRNA) | 64-128 | 32.000 | 18-22, 18-53 | 8.000 | 2 | 0.75 | Additive |

FIG. 4

| Drug | MIC (μg/mL) WT S. aureus N315 | MIC (μg/mL) PKZ18-22 resistant S. aureus N315 | Fold change in MIC |
|---|---|---|---|
| PKZ18-00 | 64 | 128 | 2 |
| PKZ18-22 | 32 | 64 | 2 |
| PKZ18-52 | 16 | 32 | 2 |
| PKZ18-53 | 32 | 64 | 2 |
| PKZ18-54 | 128 | 256 | 2 |
| Mupirocin | 0.5 | 0.5 | 1 |
| Gentamicin | 0.5 | 2 | 2.4 |
| Kanamycin | 256 | 512 | 2 |
| Neomycin | 256 | 512 | 2 |
| Streptomycin | 8 | 16 | 2 |
| Oxacillin | 0.25 | 4 | 16 |
| Tetracycline | 0.125 | 0.125 | 1 |
| Rifampicin | 0.00049 | 0.00049 | 1 |
| Chloramphenicol | 32 | 16 | 1/2 |
| Daptomycin | 4 | 4 | 1 |
| Vancomycin | 0.5 | 1 | 2 |

Increase
Decrease
No change

FIG. 6

METHOD FOR INHIBITING GROWTH OF BACTERIA

GOVERNMENT RIGHTS STATEMENT

This invention was made with Government support under grant number CHE-1929741 awarded by the National Science Foundation. The Government has certain rights in the invention.

BACKGROUND

Antibiotic resistance is acknowledged as one of the world's greatest global public health challenges. For example, the spread of hospital-acquired infections, including *Clostridioides difficile* and methicillin-resistant *Staphylococcus aureus* (MRSA), is a major concern for public health. Despite ongoing research on therapeutic treatments and prevention of bacterial, especially nosocomial, infections, current efforts for curbing antimicrobial resistance have been insufficient to overcome the problem.

Mainstays of antibiotic therapy against bacterial pathogens involve blocking bacterial growth, either by inhibiting cell wall, protein, or DNA syntheses, or by hindering critical metabolic processes. The majority of current antibiotics affect the same cellular processes that have been targeted by previous iterations of the various classes of antibiotics. Unfortunately, drug effectiveness has been severely compromised due to rapid emergence of resistance. In the case of *S. aureus*, resistance readily occurs through a variety of mechanisms, such as enzymatic inactivation, altered binding affinities, antibiotic trapping, efflux pumps, acquisition of chromosomal cassettes (mec elements), or spontaneous mutation with positive selection, in response to the exposure of each new antibiotic. Four new antibiotics were approved by the U.S. Food and Drug Administration (FDA) in 2018, but all are new iterations of antibiotics from existing classes; hence, emergence of resistance is likely. The present disclosure is directed to overcoming these and other deficiencies in the art.

Microbial biofilm formation and homeostasis constitute a major virulence factor in human infections. Biofilm-associated infections are a leading cause of morbidity and mortality in hospitalized patients. The prevalence of Gram-positive bacterial, biofilm-associated infections has increased due to the extensive use of medical implant devices. Device surfaces become colonized with Gram-positive microbes that propagate and mature into a biofilm, an immobile, sessile microbial community encased in a protective, self-produced extracellular polymeric matrix (EPM). Compared to free-floating planktonic organisms, biofilms have the characteristics of a shared physical barrier, rapid intercellular communication, and biofilm-inducible virulence factors that are employed to withstand host stress responses. This defensive EPM infrastructure, combined with a slowed metabolism, minimal replication, and emergence of multi-drug resistant bacteria, make biofilm-associated infections notoriously difficult to eradicate. Bacteria growing in a biofilm can evade the host immune system and are up to 1000-fold more resistant to antibiotic therapy compared to their planktonic counterparts. Gram-positive bacteria such as Staphylococcus aureus and streptococcal species are the most common microbes identified with biofilm-associated infections such as periprosthetic joint infections (70-80% of PJIs).

SUMMARY

The present disclosure includes improvements to address such shortcomings. In an aspect, provided is a method for inhibiting the growth of Gram-positive bacteria, including contacting said bacteria with a first compound and a second compound, wherein the first compound is a compound of Formula I:

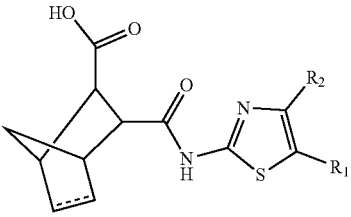

Formula I or a pharmaceutically acceptable salt thereof, wherein ⋯ represents a single or double bond; $R_1$ is selected from hydrogen and $C_{1-3}$ alkyl; and $R_2$ is selected from hydrogen, $C_{1-3}$ alkyl, a 5-membered aryl or heteroaryl ring or 6-membered heteroaryl ring wherein said 5-membered aryl or heteroaryl ring or 6-membered heteroaryl ring is optionally substituted with 1, 2, or 3 substituents individually selected from $C_{1-6}$ alkyl and halogen, and a 6-membered aryl ring optionally substituted only with a single $C_{1-6}$ alkyl substituent; and the second compound is selected from one or more of an aminoglycoside, a rifamycin, and a glycopeptide antibiotic.

In an example, ⋯ represents a single bond. In another example, ⋯ represents a double bond. In yet another example, $R_1$ is hydrogen. In still another example, $R_1$ is $C_{1-3}$ alkyl. In a further example, $R_2$ is a 6-membered heteroaryl ring optionally substituted with 1, 2, or 3 substituents individually selected from $C_{1-6}$ alkyl and halogen. In still a further example, $R_2$ is a 6-membered heteroaryl ring substituted only with a single $C_{1-6}$ alkyl substituent.

In another example, the compound of Formula I is selected from

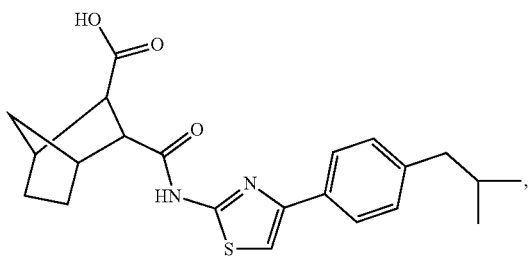

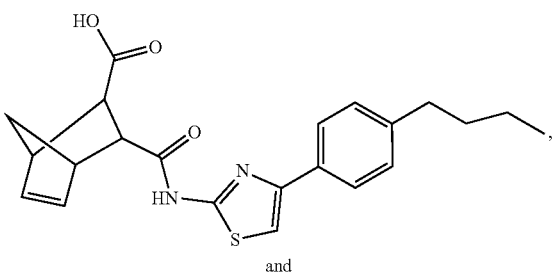

and

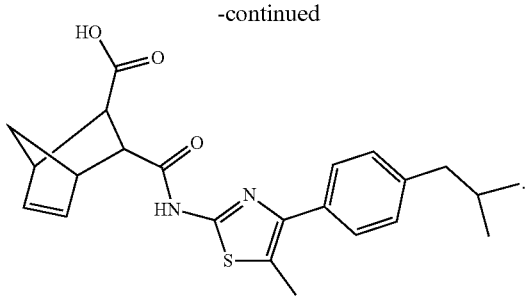

In another example, the second compound is an aminoglycoside. In an example, the aminoglycoside is selected from gentamycin, kanamycin, and neomycin. In yet another example, the second compound is a rifamycin. In an example, the rifamycin is rifampin. In still another example, the second compound is a glycopeptide antibiotic. In another example, glycopeptide antibiotic is vancomycin.

In an example, inhibiting the growth of Gram-positive bacteria includes inhibiting biofilm formation. In another example, contacting said bacteria with a first compound and a second compound includes applying said first compound and said second compound to a surface. In yet another example, applying includes applying a composition and the composition includes the first compound and the second compound. In still another example, the surface is selected from a skin of a subject, a prosthetic device, a surgical instrument, a table surface, a bench surface, and a cart surface.

In another example, the composition is selected from a cream, an ointment, and a solution. In yet another example, contacting said bacteria with said first compound and said second compound includes administering said first compound and said second compound to a subject. In another example, administering includes administering a composition and the composition includes said first compound and said second compound. In another example, administering is administering orally. In another example, administering is administering intravenously. In still another example, the composition includes a pill, a capsule, or a solution. In a further example, the composition comprises a single unit dosage.

In another aspect, provided is a pharmaceutical composition including a first compound and a second compound, wherein the first compound is a compound of Formula I:

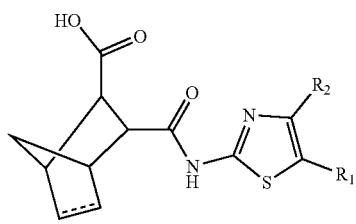

Formula I or a pharmaceutically acceptable salt thereof, wherein ----- represents a single or double bond; $R_1$ is selected from hydrogen and $C_{1-3}$ alkyl; and $R_2$ is selected from hydrogen, $C_{1-3}$ alkyl, a 5-membered aryl or heteroaryl ring or 6-membered heteroaryl ring wherein said 5-membered aryl or heteroaryl ring or 6-membered heteroaryl ring is optionally substituted with 1, 2, or 3 substituents individually selected from $C_{1-6}$ alkyl and halogen, and a 6-membered aryl ring optionally substituted only with a single $C_{1-6}$ alkyl substituent; and the second compound is selected from one or more of an aminoglycoside, a rifamycin, and a glycopeptide antibiotic.

In an example, ----- represents a single bond. In another example, ----- represents a double bond. In yet another example, $R_1$ is hydrogen. In still another example, $R_1$ is $C_{1-3}$ alkyl. In a further example, $R_2$ is a 6-membered heteroaryl ring optionally substituted with 1, 2, or 3 substituents individually selected from $C_{1-6}$ alkyl and halogen. In still a further example, $R_2$ is a 6-membered heteroaryl ring substituted only with a single $C_{1-6}$ alkyl substituent.

In another example, the compound of Formula I is selected from

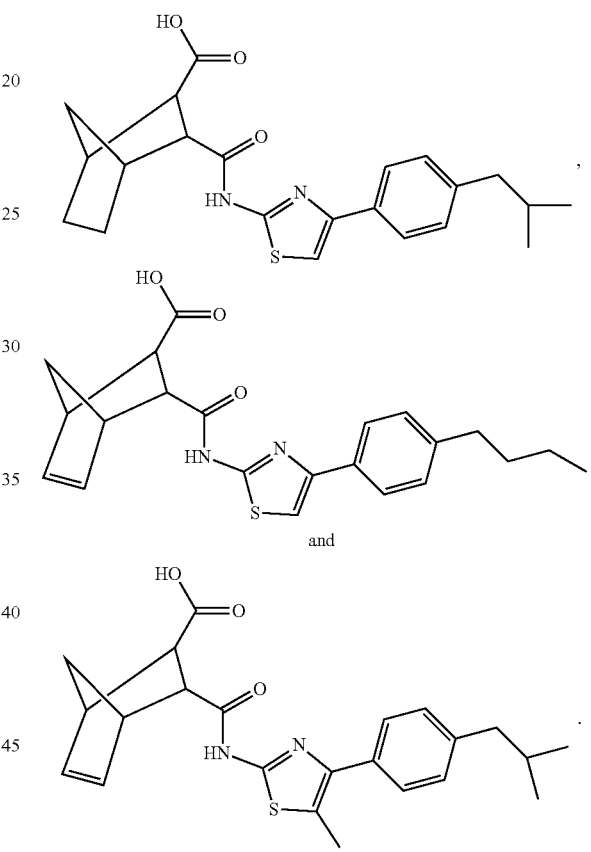

In another example, the second compound is an aminoglycoside. In an example, the aminoglycoside is selected from gentamycin, kanamycin, and neomycin. In yet another example, the second compound is a rifamycin. In an example, the rifamycin is rifampin. In still another example, the second compound is a glycopeptide antibiotic. In another example, glycopeptide antibiotic is vancomycin.

In another example, the pharmaceutical composition is selected from a cream, an ointment, and a solution. In an example, the pharmaceutical composition includes a pill, a capsule, or a solution. In a further example, the composition includes a single unit dosage.

BRIEF DESCRIPTION OF THE DRAWINGS

The patent application filed contains at least one drawing executed in color. Copies of this patent or patent application publication with colored drawings will be provided by the Office upon request and payment of the necessary fee.

These and other features, aspects, and advantages of the present disclosure will become better understood when the following detailed description is read with reference to the accompanying drawings, wherein:

FIG. 2A shows a sketch of a T-box-regulated gene layout where the two primers used for testing are represented by arrows for the T-box containing 5'UTR (left pair of primers) and the ORF (right pair of primers). FIG. 2B shows effect of PKZ18 analogs on transcriptional read-through of *B. subtilis* glyQS. Concentration is shown on the x axis, and an absence of a bar indicates no observed growth at that concentration. FIG. 2C shows side-by-side treatment of *B. subtilis* 1A5 with different PKZ18 analogs on the same biological replicate showing a direct comparison of the novel analogs' improved activity compared to PKZ18 as measured by reduced read-through of glyQS. Due to a limited amount of PKZ18-52, the bar is representative of one biological replicate. FIG. 2D shows effect of PKZ18-22 on transcriptional read-through on the T-box-regulated ileS (n=3) and tyrS (n=2) in WT MRSA.

FIG. 3A shows a heatmap of the expression of the 12 T-box controlled genes or operons in *S. aureus* and their respective 5'UTRs (T-boxes) showing a comparison of the three treatments' effect on initiation (5'UTR) and read-through (ORF). FIG. 3B shows data from panel A showing relative read-through (normalized to untreated and presented as a column graph). FIG. 3C shows a heatmap of some other 5'UTR regulated genes: SA0769 and SA0011 are regulated by SAM riboswitches, SA1173 is a sigma B regulated CDS, SA0373 is regulated by a purine riboswitch, and SA1589 is a trans-encoded sRNA. FIGS. 3D-3F show comparisons of antibiotic effect on overall change in gene expression in MRSA is shown. FIG. 3D shows 4 µg/ml PKZ18-22 to untreated, FIG. 3E shows 8µg/ml PKZ18-22 to untreated, and FIG. 3F shows 4µg/ml daptomycin to untreated.

FIG. 4 shows combinatorial effects of PKZ18 analogs with various antibiotics in accordance with aspects of the present disclosure. Class-specific antibiotics, and their respective targets are listed. The MIC and MIC with PKZ18 analog are shown, and where multiple analogs were tested, they are shown in the same cell. Fold change refers to the standalone MIC to combinatorial MIC ratio of the antibiotics tested in conjunction with PKZ18 analogs. FIC refers to the fractional inhibitory concentration, a measurement of synergy, and the value is explained in the effect column.

FIG. 5A shows J774.16 murine macrophage metabolic activity as measured by alamarBlue after 48 hours of treatment. FIG. 5B shows J774.16 murine macrophage metabolic activity as measured by alamarBlue after 72 hours of treatment. FIG. 5C shows A549 human lung epithelial cells' metabolic activity as measured by alamarBlue after 48 hours of treatment. FIG. 5D shows J774.16 murine macrophage viability measured by Trypan blue cell counting after 48 hours of treatment.

FIG. 6 shows the MICs of various drugs against WT MRSA and PKZRSA1 in accordance with aspects of the present disclosure.

FIG. 7A shows growth of *S. aureus* after 24 h exposure to PKZ18-22 vs. dosages of vancomycin in the minimum biofilm eradication (MBEC) biofilm model. Scanning electron micrographs of peg surfaces: FIG. 7B shows no treatment and FIG. 7C shows treatment with PKZ18-22.

FIG. 10 shows a synergy score matrix for drug combination of PKZ18-22 and gentamicin using a drug interaction Bliss reference model in accordance with aspects of the present disclosure. The highest drug synergy was observed with PKZ18-22 of 25 µg/mL and gentamicin concentrations of 16-64µg/mL ($p<0.001$). FIG. 11 shows a synergy score matrix for drug combination of PKZ18-22 and vancomycin. By definition all synergy scores above zero are synergistic. Synergy scores of PKZ18-22 and vancomycin exhibited significantly lower effects compared to PKZ18-22 and gentamicin. The highest synergy score for vancomycin was observed at 4µg/mL vancomycin +25 µg/mL PKZ18-22. Asterisks indicate level of confidence in results, probability of obtaining test results: * indicates $p<0.05$;  indicates $p<0.001$; * indicates $p<0.0001$. FIG. 12 shows a synergy score matrix for drug combination of PKZ18-22 and rifampin using a drug interaction Bliss model. Highest drug synergy observed with PKZ18-22 of 50 µg/mL and rifampin concentrations of 0.001-0.005 µg/mL ($p<0.001$).

FIG. 13A shows *S. aureus* biofilm CFU/log10 after 24 h of a single dose gentamicin, PKZ18-22, and the combination of gentamicin and PKZ18-22. The following asterisk values using a Student's t-test indicate: * indicates $p<0.05$; * indicates $p<0.001$. FIG. 13B** shows after a single dose 24 h challenge, the combination of gentamicin/ PKZ18-22 resulted in a cell reduction of ~5 logs, >99.9%. A significantly greater reduction when compared to each treatment alone.

DETAILED DESCRIPTION

Figure 1:
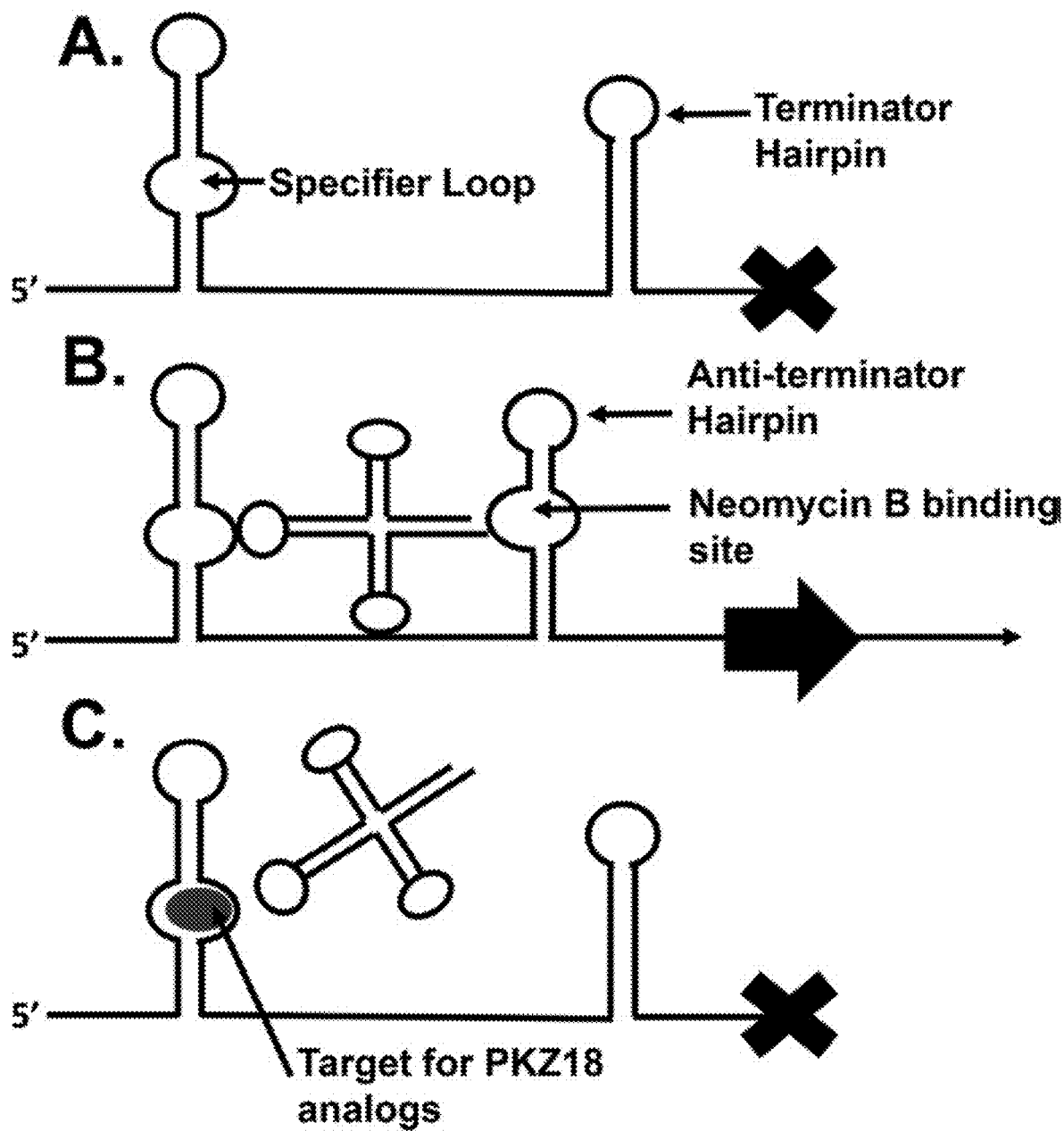
FIG. 1 shows a simplified T-box model in accordance with aspects of the present disclosure. Additional T-box hairpins and apical loop to tRNA elbow interaction are not shown. Top: An aminoacylated tRNA cannot stabilize the antiterminator helix, and the thermodynamically more stable terminator hairpin is formed, causing termination of transcription. Middle: A cognate, unacylated tRNA can stabilize the antiterminator helix, which allows transcription to continue. Bottom: PKZ analogs binding to the specifier loop prevent codon-anticodon interaction resulting in transcriptional termination.

All patents, publications, applications and other references cited herein are hereby incorporated by reference into the present application.

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, which are herein incorporated by reference in their entirety.

Unless otherwise specified, alkyl is intended to include linear, branched, and cyclic hydrocarbon structures and combinations thereof. A combination would be, for example, cyclopropylmethyl. $C_{1-6}$ alkyl groups are those having one to six carbon atoms. Examples of $C_{1-6}$ alkyl groups include methyl, ethyl, propyl, isopropyl, butyl, s-and t-butyl and the like. Cycloalkyl (which includes cyclic hydrocarbon groups) is a subset of alkyl. Examples of cycloalkyl groups include c-propyl, c-butyl, c-pentyl, norbornyl and the like.

Aryl and heteroaryl ring systems mean (i) a phenyl group (or benzene) or a monocyclic 5- or 6-membered heteroaromatic ring containing 1-4 heteroatoms selected from O, N, and S; (ii) a bicyclic 9- or 10-membered aromatic or heteroaromatic ring system containing 0-4 heteroatoms selected from O, N, and S; or (iii) a tricyclic 13- or 14-membered aromatic or heteroaromatic ring system containing 0-5 heteroatoms selected from O, N, and S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene (thiene), benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

The term "biofilm" means a group of microorganisms (one or multiple strains) surrounded by a viscous or gelatinous matrix of extracellular polymers (e.g. exopolymers or glycocalyx). These extracellular polymers are typically polysaccharides, but can also contain other biopolymers, which can be attached to either inert or biological surfaces. Standard biofilm microorganisms are bacteria that act as one or more of pathogens, indicator organisms, and spoilage organisms. Biofilm may include one or more of Gram-positive bacteria, Gram-negative bacteria, and other microorganisms. One or more composition or method disclosed herein may do or include one or more of prevent formation of biofilm, prevent growth or expansion of an existing biofilm, and reduce or remove some or all of an existing biofilm.

The term "halogen" (or "halo") means fluorine, chlorine, bromine or iodine. In one embodiment, halogen may be fluorine or chlorine.

The term "heterocyclic group" includes within its scope aromatic, non-aromatic, unsaturated, partially saturated and fully saturated heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. A particular non-limiting example is a morpholinyl group.

Radicals and substituents (Rn) are generally defined when introduced and retain that definition throughout the specification and in all independent claims.

The salt forms of the compounds of formulas (I), (II), and (III) are typically pharmaceutically acceptable salts, and examples of pharmaceutically acceptable salts are discussed in Berge et al. (1977) "Pharmaceutically Acceptable Salts," J. Pharm. Sci., Vol. 66, pp. 1-19. However, salts that are not pharmaceutically acceptable may also be prepared as intermediate forms which may then be converted into pharmaceutically acceptable salts.

The term "pharmaceutically acceptable salt" refers to salts prepared from pharmaceutically acceptable non-toxic acids or bases including inorganic acids and bases and organic acids and bases. When the compounds used in the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for compounds that may be used in the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

One or more active compound or its pharmaceutically acceptable salt or solvate in a pharmaceutical composition as disclosed herein in general is in an amount of about 0.01-20% (w/w) for a topical formulation; about 0.1-5% for an injectable formulation, 0.1-5% for a patch formulation, about 1-90% for a tablet formulation, and 1-100% for a capsule formulation.

A pharmaceutical composition may be in a dosage form such as tablets, capsules, granules, fine granules, powders, syrups, suppositories, injectable solutions, patches, or the like. A pharmaceutical composition can be an aerosol suspension of respirable particles comprising the active compound, which the subject inhales. The respirable particles can be liquid or solid, with a particle size sufficiently small to pass through the mouth and larynx upon inhalation. Examples may include particles having a size of about 1 to 10 microns, preferably 1-5 microns.

One or more active compound may be incorporated into any acceptable carrier, including creams, gels, lotions or other types of suspensions that can stabilize the one or more active compounds and deliver it to the affected area by topical applications. An above pharmaceutical composition can be prepared by conventional methods.

Pharmaceutically acceptable carriers, which are inactive ingredients, can be selected by those skilled in the art using conventional criteria. Pharmaceutically acceptable carriers may include, but are not limited to, non-aqueous based solutions, suspensions, emulsions, microemulsions, micellar solutions, gels, and ointments. Pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation including one or more active compound as disclosed herein may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation may include some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the one or more active compound as disclosed herein can be in a form of gel, cream, lotion, liquid, emulsion, ointment, spray, solution, and suspension. A one or more active ingredient in a topical formulation for example may include, but not be limited to, diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

A pharmaceutical composition as disclosed herein may be applied by systemic administration or local administration. Systemic administration may include, but is not limited to oral, parenteral (such as intravenous, intramuscular, subcutaneous or rectal), and inhaled administration. In systemic administration, the one or more active compound may first reach plasma and then be distributed into target tissues. Local administration includes topical administration.

Dosing of the composition can vary according to a level or risk of infection or bacterial growth. For systemic administration, plasma concentrations delivered of one or more active compound as disclosed herein may vary, and may include, without limitation, $1\times10^{-10}$ –$1\times10^{-4}$ moles/liter, or $1\times10^{-8}$–$1\times10^{-5}$ moles/liter, independently for each of the one or more active compound.

One or more compound as disclosed herein may be administrated orally to a subject. The dosage for oral administration may be 0.1-100, 0.1-20, or 1-50 mg/kg/day, depending on a subject's age and condition. For example, dosage for oral administration may be from 0.1-10, 0.5-10, 1-10, 1-5, or 5-50 mg/kg/day for a human subject. One or more active compound as disclosed herein may be applied orally to a human subject at 1-100, 10-50, 20-1000, 20-500, 100-800, or 200-600 mg/dosage, 1-4 times a day, independently for each of the one or more active compound.

One or more active compound as disclosed herein may be administrated intravenously to a subject. Dosage for intravenous bolus injection or intravenous infusion may be 0.03 to 5 or 0.03 to 1 mg/kg/day independently for each of the one or more active compounds.

One or more active compound as disclosed herein may be administrated subcutaneously to the subject. A dosage for subcutaneous administration may be 0.3-20, 0.3-3, or 0.1-1 mg/kg/day independently for each of the one or more active compounds.

One or more active compound as disclosed herein may be applied topically to an area and rubbed into it. A composition including one or more active compound as disclosed herein may be topically applied at least 1 or 2 times a day, or 3 to 4 times per day, depending on the medical issue and the disease pathology. A topical composition comprises about 0.01-20%, or 0.05-20%, or 0.1-20%, or 0.2-15%, 0.5-10, or 1-5% (w/w) of each of the one or more active compound, independently. In an example, 0.2-10 mL of topical composition may be applied to an individual per dose. In an example, one or more active compound as disclosed herein may pass through skin.

Those of skill in the art will recognize that a wide variety of delivery mechanisms are also suitable for the present invention.

The present invention is useful in treating a mammal subject, such as humans, horses, dogs and cats. The present invention is particularly useful in treating humans.

The following examples further illustrate the present invention. These examples are intended merely to be illustrative of the present invention and are not to be construed as being limiting.

This disclosure relates to compositions and methods for inhibiting the growth of Gram-positive bacteria. Compositions include a first compound of Formula I and a second compound selected from one or more of an aminoglycoside, a rifamycin, and a glycopeptide antibiotic. Methods include contacting the Gram-positive bacteria with such first compound and such second compound. As disclosed herein, in examples contacting bacteria with such a first compound and such a second compound synergistically inhibits growth of the bacteria, such that an inhibitory effect on bacterial growth is more than a summation of effects of contacting a bacterium with each of the compounds without contacting the bacteria with the other of the compounds. Inhibitory effects of some non-limiting examples of compounds of Formula I on growth of bacteria are disclosed in U.S. Pat. No. 10,266,527, the entire contents of which is incorporated herein in its entirety.

The riboswitch is a 5'-untranslated region (5'UTR) of a messenger RNA (mRNA) with a binding site for a ligand specific to that message. Binding of the ligand controls expression of the protein encoded by that mRNA via regulating transcription or translation. A riboswitch undergoes dynamic exchange between alternative conformations, each of which leads to a different biological result. Depending on the mRNA and its genetic regulation, the ligand can be a positive or negative effector of protein synthesis. A number of genes crucial to metabolite biosynthesis or transport are regulated in bacteria through the binding of the cognate metabolites to classes of mRNA riboswitches. As disclosed herein, riboswitches may be fundamentally alternative RNA drug targets because they have evolved over millions of years as structured receptors for the purpose of binding ligands. As a consequence, riboswitches form ligand-receptor interfaces with a level of structural complexity and selectivity that approaches that of proteins. In some bacterial pathogens, the downstream genes regulated by a riboswitch are essential for bacterial survival and virulence. Therefore, designing small molecules targeting this kind of riboswitch may yield a lethal effect to bacterial pathogens.

Several riboswitches are unique to bacterial pathogens, and not found in humans. Similar to antibiotic resistance for protein-based targets, bacteria may also evolve resistance to riboswitch-targeting drugs through a mutation that disrupts binding to the riboswitch receptor. However, it may be difficult for a pathogen to evolve selective resistance to riboswitch-targeting antibiotics via a point mutation in the riboswitch. Reasons may include: (1) point mutations in riboswitches would also disrupt the native metabolite ligand binding, resulting in deregulation of the associated biosynthetic pathways; and (2) when several riboswitches of the same class are targeted by a single compound, mutations in each riboswitch would be necessary to produce resistance.

Maintenance of appropriate pools of aminoacylated tRNAs for protein synthesis is essential for bacterial viability. This requires not only balanced levels of tRNAs, but also their cognate aminoacyl-tRNA synthetases (aaRSs) that catalyze the tRNA aminoacylation. In Gram-positive bacteria, including MRSA, transcription of most aaRS genes is uniquely regulated by the specific tRNA substrate binding to the 5'UTR of the nascent mRNA. Though the size of tRNA as a regulatory ligand contrasts greatly with the more common small metabolite-regulated riboswitches, the tRNA-dependent riboswitch operates similarly in that the completion of transcription is controlled through a resulting conformational change. Similar to other T-box family genes, the 5'UTR of the mRNA of the regulated aaRS gene exhibits a conservation of sequence and structural features. Segments of 5'UTR RNA can fold to form two alternative hairpin structures, an intrinsic transcription terminator or a competing transcription anti-terminator. Formation of the terminator hairpin prematurely terminates transcription.

As disclosed herein, unacylated tRNA may be a positive effector of this regulatory riboswitch in its binding to the 5'UTR of the nascent mRNA, stabilizing the anti-terminator conformation, and leading to transcription of the downstream aaRS gene. Specificity of this 5'UTR:tRNA interaction may be determined, at least in part, by pairing of the tRNA's specific anticodon with a complementary codon sequence in the specifier loop, whereas stabilization of the anti-terminator may be dependent on base-pairing of the universal tRNA terminal (5'-NCCA-3') with complementary residues (5'-UGGN-3') in a 7-nt bulge of the anti-terminator. In response to a decreased pool of aminoacylated tRNA, unacylated tRNA recognized by the nascent transcript may result in increased expression of aaRS genes, which continue to aminoacylate more tRNAs. A covalently bound amino acid of an aminoacylated tRNA may negate tRNA binding to the nascent mRNA and thus, an intrinsic terminator helix is formed and transcription is relinquished prior to the coding sequence of the mRNA.

A specifier loop domain is located in the Stem I of the 5'UTR and contains nucleotides that are complementary to and pair with the tRNA anticodon. Stem I has two major common RNA structural motifs (loop E and K-turn motifs) and both are crucial for proper transcriptional regulation. The loop E motif in the specifier loop provides a stable platform that appears to help position the specifier nucleotides to accept the anticodon of the cognate tRNA. This motif is similar to that found in several prokaryotic and eukaryotic rRNAs and the hairpin ribozyme. The NMR-derived structure of a model Stem I in the 5'UTR of the tyrosyl-tRNA synthetase (tyrRS) mRNA supports the presence of the Loop E motif in the specifier loop. The single-strand specifier nucleotides stack with their Watson-Crick edges displaced toward the minor groove. The K-turn, or GA, sequence motif is joined to the specifier loop domain by a 3-to 5-bp helix. The NMR structure showed the K-turn sequence motif has several noncanonical base pairs typical of K-turn structures, but adopts an extended conformation. These motifs may create an intricate folding pocket in the specifier loop. The overall structure of the specifier loop may be well ordered, with only a few nucleotides exhibiting a moderate degree of mobility. The specifier nucleotide bases are stacked, but their Watson-Crick edges are not uniformly displayed. The 3'-two bases are rotated toward the minor groove and readily accessible to the tRNA anticodon, whereas the 5'-base is rotated toward the major groove with its base pairing edges pointing toward the helix axis.

As the specific recognition of the cognate unacylated tRNA can occur in the absence of any other cellular factors for the glycyl-tRNA synthetase (glyQS) 5'UTR, determining the structure of the specifier loop of the glyQS riboswitch in the complex with tRNA may provide more relevant and accurate structural information for a novel therapeutic drug target. Disrupting tRNA:5'UTR interaction by targeting mRNA with a small molecule may result in the riboswitch conformation in the OFF position. Small molecule intervention would negate transcription of the downstream aaRS gene, and aaRS proteins critical to the pathogen's viability would not be synthesized, preventing further infection.

Without wishing to be bound by theory, the binding of small compounds to the glyQS stable platform region is thought to either deform the specifier loop or prevent the conformational change necessary for interaction with the anticodon and thus, inhibit the interaction of the nascent transcript with the tRNA. Transcription of the aaRS gene is then terminated.

Compounds of Formula I as disclosed herein are believed to perturb the interaction of the specifier loop and tRNA anticodon stem and loop of a T-box riboswitch unique to Gram-positive bacteria and therefore, may be useful in the treatment of infection caused by Gram-positive bacteria.

Referring to FIG. 1, Specific tRNAs initially bind to a cognate codon in the specifier loop. An unacylated cognate tRNA may then stabilize an antiterminator helix in the mRNA downstream of stem I through base-pairing interactions with the conserved 3' NCCA acceptor end of the tRNA and a conserved complementary sequence 5'-UGGN of the mRNA, the "T-box," thus, allowing the RNA polymerase to continue transcription (FIG. 1, middle). Conversely, charged or even slightly modified tRNA cannot stabilize the antiterminator helix, causing the thermodynamically more stable terminator hairpin to form and transcription to halt.

Inhibitory effects of some non-limiting examples of compounds of Formula I on growth of bacteria are disclosed in U.S. Pat. No. 10,266,527, the entire contents of which is incorporated herein in its entirety. Some non-limiting examples compounds, including but not limited to some compounds of Formula I, as disclosed herein are shown in Table 1:

TABLE 1

Examples of compound structures:

| PKZ Analog Number | $R_3$ | $R_4$ | $R_5$ | T-Box targeting[a] |
|---|---|---|---|---|
| PKZ 18-00 | $R_3$—$CH_3$ | isopropyl ($R_4$ with two $CH_3$) | norbornane with OH, C=O | Yes |
| PKZ 18-21 | $R_3$—H | isopropyl ($R_4$ with two $CH_3$) | norbornane with OH, C=O | Yes |
| PKZ 18-22 | $R_3$—H | isopropyl ($R_4$ with two $CH_3$) | norbornane with OH, C=O | Yes |
| PKZ 18-52 | $R_3$—$CH_3$ | $R_4$—propyl—$CH_3$ | norbornene with OH, C=O | Yes |

TABLE 1-continued

Examples of compound structures:

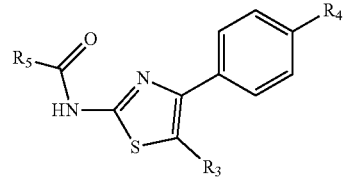

| PKZ Analog Number | R₃ | R₄ | R₅ | T-Box targeting[a] |
|---|---|---|---|---|
| PKZ 18-53 | R₃—CH₃ | 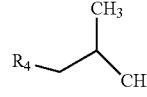 | 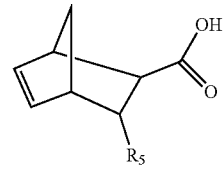 | Yes |
| PKZ18-54 | R₃—CH₃ | 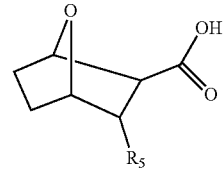 | 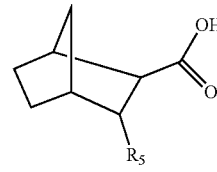 | No |
| PKZ 18-55 | R₃—H | 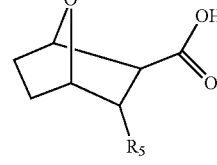 | 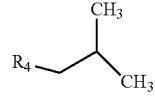 | No |
| PKZ 18-56 | R₃—CH₃ | 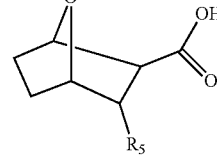 | 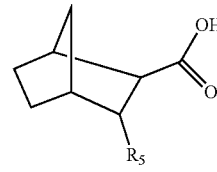 | No |
| PKZ 18-57 | R₃—CH₃ | 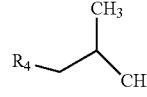 | 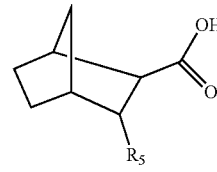 | No |
| PKZ 18-58 | R₃—H | 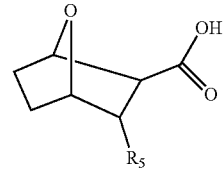 | 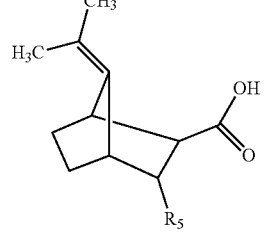 | No |

[a] = Confirmation of inhibition of T-box mechanism from qRT-PCR assay.

Disclosed are compositions including a first compound, of Formula I, and a second compound, wherein the second compound may be any antibiotic other than a compound of Formula I. In an example, the second compound may be one or more of an aminoglycoside, a rifamycin, and a glycopeptide antibiotic. Also provided is a method of inhibiting growth of Gram-positive bacteria, including contacting the bacteria with said first compound and said second compound. In an example, said first compound and said second compound may be considered an active pharmaceutical ingredient or an active pharmaceutical agent. Examples may include administering one or more composition including one or more compound as disclosed herein to a subject.

In an example, a composition may include both of said first compound (i.e. a compound of Formula I) and said second compound (i.e., antibiotic other than a compound of Formula I). In another example, one or more examples of said first compound may be included in a first composition, and one or more of said second compound may be included in a second composition, and said first composition and said second composition may be separate compositions from each other. In accordance with a method as disclosed herein, said first composition and said second composition may both be used for contacting a microorganism such as a bacterial species with said first and second compounds. Or, a single composition including one or more of said first compound and one or more of said second compound may be used for contacting a microorganism such as a bacterium with said first and second compounds. Such one or more compounds may include, independently, and ointment, a cream, a pill, an injectable, a patch, a cleaning solution (such as for application to a surface), or any other example as disclosed herein.

Compounds as disclosed herein may be applied to any biological or non-biological surface for inhibiting growth of bacteria, such as Gram-positive bacteria. A biological surface may include any exterior surface of a subject (such as skin, orifice, or open wound) or internal surface of a subject (such as of an alimentary or other canal, a bladder, a duct, a vessel, a fascia, an osseous or cartilaginous surface including periosteal and endosteal surfaces, an internal organ or tissue membrane, a cavity, a ventricle, or other internal surface). A surgical or other wound, opening, or stoma in the skin or other biological membrane, including without limitation for a transcutaneous implant, catheter (e.g. PICC line), port, etc., may be contacted or cleaned with one or more composition including one or both type of compound as disclosed herein. A biological internal surface may be contacted by administering one or more composition systemically to a subject. A non-biological surface may include any surface on which a biofilm may form, including furniture, a cart, a tray, a bin, a pan, surgical tools or implements such as may be present in a surgical setting, gloves, drapes, curtains, clothes, footwear, walls, doors, floors, pipes, sinks, faucets, knobs, handles, handrails, lights, machines, electrical instruments, counters, seats, foodware, or any other surface. A non-biological surface may include a surface of an object for implant or insertion to a subject, such as any prosthetic, a needle, a guide, a catheter or line, a port, a pump, a monitor, a pin, a screw, a joint, an electrode, a stent, a tube, an aperture or window for monitoring or visualizing tissue or other subcutaneous tissue, a capsule, a camera, or other object.

A method or composition as disclosed herein may include one or more of a first compound of Formula I and a second compound which second compound is an antibiotic other than a compound of Formula I. More than one compound of Formula I may be included, as may more than one antibiotic that is not a compound of Formula I. An antibiotic other than a compound of Formula I may include an aminoglycoside, such as amikacin, gentamicin, kanamycin, neomycin, netilmicin, tobramycin, paromomycin, streptomycin, spectinomycin, or another aminoglycoside. An antibiotic other than a compound of Formula I may include an ansamycin, such as geldanamycin, herbimycin, refimixin, or another ansamycin. An antibiotic other than a compound of Formula I may include a carbacephem, such as loracarbef, or another carbacephem. An antibiotic other than a compound of Formula I may include a carbapenem, such as ertapenem, doripenem, imipenem/cilastatin, meropenem, or another carbacephem.

An antibiotic other than a compound of Formula I may include a cephalosporin, including a first-, second, third-, fourth, or fifth-generation cephalosporin, such as cefadroxil, cefazolin, cephradine, cephapirin, cephalothin, cefalexin, cefaclor, cefoxitin, cefotetan, cefamandole, cefmetazole, cefonocid, loracarbef, cefprozil, cefuroxime, cefixime, cefdinir, cefditoren, cefoperazone, cefotaxime, cefpodoxime, ceftadizime, ceftibuten, ceftizoxime, moxalactam, ceftriaxone, cefepime, ceftaroline fosamil, ceftobiprole, or another cephalosporin.

An antibiotic other than a compound of Formula I may include a glycopeptide, such as teicoplanin, vancomycin, telavancin, dalbavancin, oritavancin, or another glycopeptide. An antibiotic other than a compound of Formula I may include a lincosamide, such as clindamycin, lincomycin, or another lincosamide. An antibiotic other than a compound of Formula I may include a lipopeptide, such as daptomycin or another lipopeptide. An antibiotic other than a compound of Formula I may include a macrolide, such as azithromycin, clarithromycin, erythromycin, roxithromycin, telithromycin, spiramycin, fidaxomicin, or another macrolide. An antibiotic other than a compound of Formula I may include a monobactam, such as aztreonam or another monobactam. An antibiotic other than a compound of Formula I may include a nitrofuran, such as furazolidone, nitrofurantoin, or another nitrofuran. An antibiotic other than a compound of Formula I may include an oxazolidinone, such as linezolid, posizolid, radezolid, torezolid, or another oxazolidinone.

An antibiotic other than a compound of Formula I may include a penicillin, such as amoxicillin, ampicillin, azlocillin, dicloxacillin, flucloxacillin, mezlocillin, methicillin, nafcillin, oxacillin, penicillin G, penicillin V, piperacillin, penicillin G, temocillin, ticarcillin, or another penicillin. An antibiotic other than a compound of Formula I may include a penicillin combination, such as amoxicillin/clavulanate, ampicillin/sulbactam, piperacillin/tazobactam, ticarcillin/clavulanate, or another penicillin combination.

An antibiotic other than a compound of Formula I may include a polypeptide, such as bacitracin, colistin, polymyxin B, or another polypeptide. An antibiotic other than a compound of Formula I may include a quinolone/fluroroquinolone, such as ciprofloxacin, enoxacin, gatifloxacin, gemifloxacin, levofloxacin, lomefloxacin, moxifloxacin, nadifloxacin, nalidixic acid, norfloxacin, ofloxacin, trovafloxacin, grepafloxacin, sparfloxacin, temafloxican, or another quinolone/fluroroquinolone. An antibiotic other than a compound of Formula I may include a sulfonamide, such as mafenide, sulfacetamide, sulfadiazine, silver sulfadiazine, sulfadimethoxine, sulfamethizole, sulfamethoxazole, sulfanilimide, sulfasalazine, sulfasoxazole, trimethoprim-sulfamethoxazole (Co-trimoxazole) (TMP-SMX), sulfonamidochrysoidine, or another sulfonamide. An antibiotic other than a compound of Formula I may include a tetracycline, such as demeclocycline, doxycycline, metacycline, minocycline, oxytetracycline, tetracycline, or another tetracycline.

An antibiotic other than a compound of Formula I may include an anti-mycobacterial compound, such as clofazimine, dapsone, capreomycin, cycloserine, ethambutol, ethionamide, isoniazid, pyrazinamide, a rifamycin (such as rifampin, rifabutin, rifapentine, or rifaximin, or another rifamycin), streptomycin, or another anti-mycobacterial compound. An antibiotic other than a compound of Formula I may include arsphenamine, chloramphenicol, fosfomycin, fusidic acid, metronidazole, mupirocin, platensimycin, quinupristin/dalfopristin, thiamphenicol, tigecycline, tinidazole, trimethoprim, or another antibiotic other than a compound of Formula I.

All combinations of one or more of all compounds of Formula I and of one or more of all antibiotics other than a compound of Formula I are explicitly included in compositions disclosed herein and for use in methods disclosed herein and can be easily envisioned by any skilled person from the foregoing.

In an example, the first compound includes any one or more of, or a pharmaceutically acceptable salt of any one or more of,

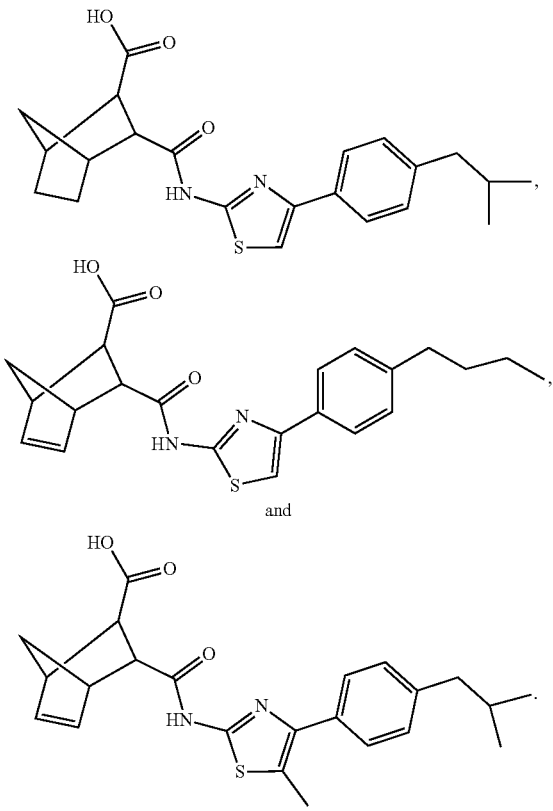

In an example, the compound including the antibiotic other than a compound of Formula I includes one or more of gentamycin, kanamycin, neomycin, rifamycin, and vancomycin. All combinations of one or more of these compounds of Formula I and one or more of these antibiotics other than Formula I are explicitly included in compositions as disclosed herein and for use in methods as disclosed herein and can easily by envisioned by a skilled person on the basis of the foregoing. A combination may include

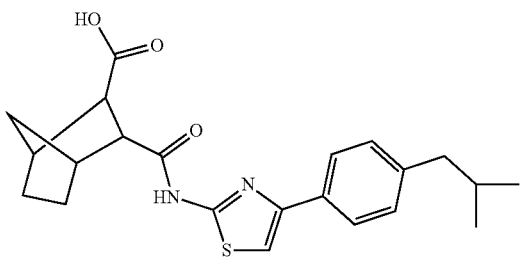 [SMILES: CC(C)Cc1ccc(-c2csc(NC(=O)C3C4CCC(C4)C3C(=O)O)n2)cc1]

and gentamycin, kanamycin, neomycin, rifamycin, and vancomycin, or

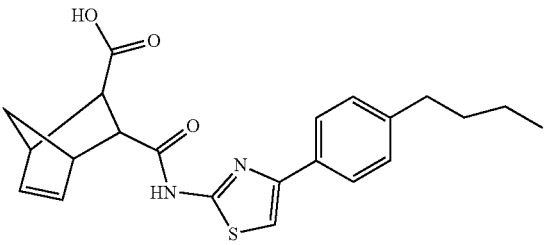 [SMILES: CCCCc1ccc(-c2csc(NC(=O)C3C4C=CC(C4)C3C(=O)O)n2)cc1]

and gentamycin, kanamycin, neomycin, rifamycin, and vancomycin, or

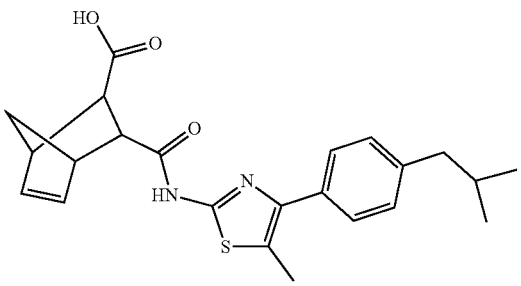 [SMILES: Cc1sc(NC(=O)C2C3C=CC(C3)C2C(=O)O)nc1-c1ccc(CC(C)C)cc1]

and gentamycin, kanamycin, neomycin, rifamycin, and vancomycin, as nonlimiting examples.

Inhibiting growth of bacteria may be ascertained by measuring an amount of bacteria before and after a period of time during which the bacteria are not contacted with a compound of Formula I or other antibiotic other than a compound of Formula I to identify an amount of bacterial growth in the absence of a compound of Formula I and another antibiotic other than a compound of Formula I, measuring an amount of bacteria before and after a period of time during which the bacteria are contacted with a compound of Formula I and another antibiotic other than a compound of Formula I to identify an amount of bacterial growth in the presence of a compound of Formula I and another antibiotic other than a compound of Formula I, and comparing the amount of bacterial growth in the absence of a compound of Formula I and another antibiotic other than a compound of Formula I with the amount of bacterial growth in the presence of a compound of Formula I and another antibiotic other than a compound of Formula I. An amount of inhibition of bacterial growth is the difference between the former and the latter when the latter is less than the former. Growth in the presence of only one or the other of a compound of Formula I and an antibiotic other than a compound of Formula I may similarly be ascertained and compared to the amount of bacterial growth in the absence of a compound of Formula I and another antibiotic other than a compound of Formula I with the amount of bacterial growth in the presence of a compound of Formula I and another antibiotic other than a compound of Formula I. A synergistic effect of a compound of Formula I and an antibiotic other than a compound of Formula I may occur when the amount of inhibition of bacterial growth in the presence of a compound of Formula I and another antibiotic other than a compound of Formula I is greater than the sum of the amount of inhibition of bacterial growth in the presence of a compound of Formula I and absence of an antibiotic other than a compound of Formula I and the amount of inhibition of bacterial growth in the presence of an antibiotic other than a compound of Formula I and absence of a compound of Formula I.

Inhibiting growth of biofilm may be ascertained by measuring an amount of biofilm before and after a period of time during which the biofilm is not contacted with a compound of Formula I or other antibiotic other than a compound of Formula I to identify an amount of biofilm growth in the absence of a compound of Formula I and another antibiotic other than a compound of Formula I, measuring an amount of biofilm before and after a period of time during which the biofilm is contacted with a compound of Formula I and another antibiotic other than a compound of Formula I to identify an amount of biofilm growth in the presence of a compound of Formula I and another antibiotic other than a compound of Formula I, and comparing the amount of biofilm growth in the absence of a compound of Formula I and another antibiotic other than a compound of Formula I with the amount of biofilm growth in the presence of a compound of Formula I and another antibiotic other than a compound of Formula I. An amount of inhibition of biofilm growth is the difference between the former and the latter when the latter is less than the former. Growth in the presence of only one or the other of a compound of Formula I and an antibiotic other than a compound of Formula I may similarly be ascertained and compared to the amount of biofilm growth in the absence of a compound of Formula I and another antibiotic other than a compound of Formula I with the amount of biofilm growth in the presence of a compound of Formula I and another antibiotic other than a compound of Formula I. A synergistic effect of a compound of Formula I and an antibiotic other than a compound of Formula I may occur when the amount of inhibition of biofilm growth in the presence of a compound of Formula I and another antibiotic other than a compound of Formula I is greater than the sum of the amount of inhibition of biofilm growth in the presence of a compound of Formula I and absence of an antibiotic other than a compound of Formula I and the amount of inhibition of biofilm growth in the presence of an antibiotic other than a compound of Formula I and absence of a compound of Formula I.

EXAMPLES

The following examples are intended to illustrate particular examples of the present disclosure, but are by no means intended to limit the scope thereof Materials and Methods All chemicals, including novel PKZ18 analogs, were obtained from commercial sources. Novel analogs were selected based on availability and semblance to PKZ18 and PKZ18-22. All antimicrobials were resuspended in dimethyl sulfoxide (DMSO) unless otherwise specified and verified by mass spectrometry (MS).

Strains and Media

A549 human lung epithelial cells (grown in Ham's F12 media [Gibco] with 0.00146 g/liter L-glutamine and 10% fetal bovine serum [FBS; Gibco] added) and J774.16 murine macrophages (grown in J7 media with 74% Dulbecco's modified Eagle medium [DMEM; Gibco]) with 0.584 g/liter L-glutamine added, 20% FBS, 5% NCTC-109 [Gibco], and 1% nonessential amino acids) were used for cytotoxicity assays. The following bacterial strains were used in the assays: *Bacillus subtilis* 168, *Bacillus subtilis* 1A5, *Staphylococcus aureus* 4220, *Staphylococcus aureus* N315 (MRSA isolate), and *Escherichia coli* BL21. *Bacillus subtilis* 1A5 and *S. aureus* N315 were used in qRT-PCR experiments. The abovementioned bacterial strains were used in other experiments as specified. Bacteria were grown on plain Luria-Bertani (LB) or brain heart infusion (BHI) agar except for MRSA, which was grown on BHI agar with 20 μg/ml erythromycin. Liquid cultures were grown in BHI or minimal media (Spizizen minimal medium for *B. subtilis* and SSM9PR [60] for *S. aureus*) with the desired antibiotic or solvent control.

Primers

Sample preparation of RNA and cDNA. RNA extraction and cDNA preparation were conducted as previously reported. In short, guanidine thiocyanate (0.5 M final concentration)-treated and pelleted bacterial cultures were resuspended in TRIzol, lysed by beat beating with zirconia beads, and centrifuged.

The solution was transferred to fresh tubes, and the RNA was extracted with chloroform. The RNA was then pelleted with 100% isopropanol and washed with ice-cold 70% ethanol, resuspended in Millipore water, DNase treated, and extracted with another isopropanol precipitation and ethanol wash. The resulting RNA was quantified using a NanoDrop 3300 (Thermo Fisher), and the quality was assessed by running 1 μg on a denaturing agarose gel. DNA contamination was tested for by PCR followed by agarose gel electrophoresis. cDNA was generated from 1 μg of high-quality RNA using the SuperScript III reverse transcriptase protocol for random primers (Thermo Fisher).

Thermodynamic Stability Measurements with PKZ18 Analogs

Thermodynamic parameters were derived from four UV-monitored destabilizations and four renaturations of chemically synthesized wild-type and mutant truncated *B. subtilis* glyQS Stem I specifier loops in the absence and presence of PKZ18 (10 mM $Na_2HPO_4$ and 10 mM $KH_2PO_4$; final pH 6.8). The absorbance was collected at 260 nm and was performed using a Varian Cary 3 UV-visible spectrophotometer equipped with a Peltier temperature control accessory. The temperature was increased at a rate of 1° C. per minute from 5 to 85° C. Absorbance data at 260 nm were collected as a function of temperature at a rate of four data points per minute. All experiments were performed simultaneously with a control cell containing buffer only. The error calculated is the error of the mean.

qRT-PCR

Either 2-fold or 10-fold dilutions of cDNA were used, and amplification was monitored with Evagreen dye. The expression was normalized to either 23S (*B. subtilis* 1A5) or 16S (MRSA) and reported as percentage read-through of the T-boxes tested for, calculated using the threshold cycle ($2^{-\Delta\Delta C_T}$) method.

Minimum Inhibitory and Bactericidal Concentration Determinations

MICs were determined essentially as previously described (Frohlich KM, Weintraub SF, Bell JT, Todd GC, Väre VYP, Schneider R, Kloos ZA, Tabe ES, Cantara WA, Stark CJ, Onwuanaibe UJ, Duffy BC, Basanta-Sanchez M, Kitchen DB, McDonough KA, Agris PF. 2019. Discovery of small-molecule antibiotics against a unique tRNA-mediated regulation of transcription in Gram-positive bacteria. ChemMedChem 14:758-769.). In short, cultures were grown overnight in the appropriate media, diluted to $A_{620}$ of 0.1, grown for 3 hours, and again diluted to $A_{620}$ of 0.1. Cultures were then diluted 10-fold, of which 5 µl were added to each well of the 96-well plate used for the experiment except the media control wells. The initial well inoculum was $7.5 \times 10^5$ bacteria for *S. aureus* and $2.5 \times 10^5$ bacteria for *B. subtilis* (bacterial numbers were measured by OD). The 96-well plate was organized as follows. Media (100 µl) were added to all wells. Stock solutions (100 µi) containing 2 times the highest concentration of antibiotics to be tested were loaded to column 1, with two technical repeats per drug. The plate was serially diluted 2-fold from left to right, and media after the last dilution were discarded, so each well had a final volume of 100 µl. The following controls were included: vehicle control (DMSO, chloroform, ethanol, etc.), cells in plain media, and media control (no cells). The initial optical density ($A_{620}$) of the 96-well plate was determined, the plate was grown for 16 to 24 hours, and at that time, the final optical densities ($A_{620}$) were read. The initial reading was subtracted from the final reading, and the technical replicates were averaged. MICs of PKZ18 and analogs were compared to clinically used antibiotics such as gentamicin.

For minimal bactericidal concentration (MBC) testing, the wells from the above 96-well plate, which showed no growth, were plated on drug-free rich media agar plates and incubated for 16 to 24 hours, at which point they were imaged and colonies were counted.

alamarBlue Cell Redox Activity alamarBlue was purchased (Thermo Scientific) and used according to the manufacturer's directions. In short, 50,000 cells of either A549 or J774.16 were added into a 96-well plate in 200 µl and left to adhere overnight. As a control, we used a 96-well plate with the desired drugs at 2× the final concentrations in 160 µl without adding cells. The cells' medium was removed, and 100 µl fresh medium was added, followed by 100 µl of 2× drug from the corresponding wells in the drug plate. Media were added to the drug plate to reduce the concentrations to 1×, and the cells were incubated at 37° C. for 48 or 72 hours. alamarBlue was added at 10 µl per 100 µl, and the fluorescence of both plates at 590 nm was read after overnight incubation. The drug plate fluorescence was subtracted from the cells' plate respective values, and the data were normalized to untreated cells' reading. All plates included a vehicle control used as the 0-µg/ml value for each drug tested. All concentrations were tested in triplicate and included at least three biological replicates. A media control, untreated control, a killing control, and a vehicle control were always included. The cytotoxicity of synergistic or additive MICs of PKZ18 analogs and a common antibiotic (co-MIC) on eukaryotic cells was tested on A549 cells as above, but the two plates were set up identically to the checkerboard assay so that the final concentrations tested corresponded to those tested against MRSA.

Trypan Blue Cell Viability Counting

J774.16 cells were grown in J7 medium from a fresh passage in a 1:4 dilution of 70 to 80% confluent cells. The cells were allowed to adhere in 6-well plates overnight. The medium was replaced, and drugs were added to desired concentrations in a total volume of 5 ml/well. A media control, untreated control, a killing control of Triton X-100, and a vehicle control were always included. After 48 hours treatment, medium was removed, and fresh media and Trypan blue were added 1:1 in a final volume of 400 µl. Cells, 100 to 200, from two areas of each well were counted and the data averaged and normalized against untreated cells. The vehicle control served as the 0.0-µg/ml value. At least three biological replicates were included for each drug at each concentration.

Checkerboard Assay and FIC

*S. aureus* N315 cultures were prepared identically to MIC determination in BHI media. The co-MICs were determined using the checkerboard method. In short, antibiotics to be tested with PKZ18 analogs were diluted 2-fold top to bottom (A to G rows) in a 96-well plate, PKZ18 analogs were diluted 2-fold right to left (columns 11-2 of the 96-well plate), and column 12 was used for vector, media, and growth controls. Each drug was therefore tested by itself and with every dilution of the other drug.

The synergistic and additive interactions were determined based on determined cutoffs using the equation $$FIC = \frac{MIC_{AB}}{MIC_A} + \frac{MIC_{AB}}{MIC_B}$$

where $MIC_{AB}$ is the lowest possible concentration of both drugs combined where there is no growth, and $MIC_A$ and $MIC_B$ are the MIC values of the individual drugs. For a synergistic drug interaction, the fractional inhibitory concentration (FIC) should be below 0.5, additive or indifferent effects are considered in an FIC range of 0.5 to <4, and an FIC value above 4 is considered antagonistic.

Antibiotic Resistance Frequency (Fluctuation Assay

Fluctuation assays were performed using *S. aureus* N315 and *B. subtilis* 168 with both PKZ18-22 and PKZ18 on BHI agar plates. Gentamicin on BHI agar was used as a control. In short, MRSA and *B. subtilis* were grown overnight in BHI, and 3-hour day cultures at the optical density of $A_{620}$ of 0.1 were started for both organisms. The optical density after 3 hours of growth was measured; cultures were then pelleted and resuspended to give $10^{11}$ CFU/ml by optical density. CFU of $10^{11}$ per OD were plated in total; 100 µl of the cells were then plated on BHI agar containing either 128 µg/m1PKZ18 or 64 µg/m1PKZ18-22. Serial dilutions of the cells were plated on plain BHI agar in order to calculate the CFU/ml, which was calculated as the number of colonies found on the plates divided by the total number of bacteria plated. CFU means colony forming units, a measure of live bacteria.

Efflux Activity

Efflux activity of the PKZ18-22-resistant MRSA was compared to WT N315. Briefly, cultures were resuspended in phosphate-buffered saline (PBS) and loaded with ethidium bromide for 30 minutes. The cells were then resuspended in cold PBS and transferred onto a 96-well plate in the presence or absence of efflux inhibitors (100 µM carbonyl cyanide m-chlorophenylhydrazone [CCCP] or Verapamil) and 0.4% glucose, and the efflux activity was monitored by measuring the fluorescence of ethidium bromide every 60 seconds for 60 minutes. The activity was normalized to the highest fluorescence reading observed.

Kill Curves for Resistance Testing

WT MRSA and resistant strains were grown overnight in BHI and diluted to an optical density of $A_{620}$ of 2.0, and both strains were split into three 10-ml cultures with either 64 or 128 µg/ml of PKZ18-22 or 10 µg/ml vancomycin added. The optical density at 620 nm was taken every hour for the first 6 hours and a final time point after 24 hours. Dilutions of 0-, 3-, 6-, and 24-h samples of PKZ18-22 treated cultures were plated on BHI agar to determine total CFU of bacteria.

RNA Sequencing and Bioinformatic Analyses

MRSA and resistant strains were grown overnight in BHI and diluted to an optical density of $A_{620}$ of 2.0, and both strains were split into three 10-ml cultures with either 64 or 128 µg/ml of PKZ18-22 or 10 µg/ml vancomycin added. The optical density at 620 nm was taken every hour for the first 6 hours and a final time point after 24 hours. Dilutions of 0-, 3-, 6-, and 24-h samples of PKZ18-22 treated cultures were plated on BHI agar to determine total CFU of bacteria.

Determining if Biofilm Formation is Susceptible to PKZ18 Analogs In Vitro

Biofilm formation starts from planktonic bacteria, followed by adhesion to an organic or abiotic surface. Following the initial adhesion, sessile microcolonies form and extracellular polymeric substance (EPS) is secreted. Bacteria embedded in EPS often enter a "stationary-like" phase or persister status, making them less susceptible to conventional antibiotics that target growing cells. An overnight culture of S. aureus (ATCC 29213) was diluted to 1×10⁷ cells/mL in tryptic soy broth (TSB) supplemented with 10% human plasma (Innovative Research, Novi, Mich. USA) and added to the wells of an MBEC™-HTP Assay Biofilm Innoculator (Innovotech, Edmonton, AB, Canada). The plate was incubated overnight at 37° C. and shaken at 125 rpm. After 24 h of growth the lid of the plate was removed, rinsed with PBS, and transferred to a standard 96-well plate containing dilutions of PKZ18-22 and vancomycin prepared in TSB. Control wells were without a COMPOUND OF Formula I. The treatment plate was incubated for 24 h at 37° C. after which the lid was removed, rinsed with PBS, and placed in a new 96-well plate containing TSB. The biofilm was removed from the assay lid into the recovery plate wells by sonication, a new plate cover was added, and the viability of the biofilm was determined after 24 h of incubation at 37° C. by reading the OD at 625 nm. Three independent experiments were conducted. Concentrations of interest were followed up with colony forming unit (CFU) recovery and scanning electron microscopy analysis. After conclusion of the MBEC assay, the minimum bactericidal concentration (MBC) was determined. The MBC is the lowest concentration of an antibacterial agent required to kill a particular bacterium. The peg lid from the MBEC assay was removed from the challenge plate and 20 µL of medium from each well of the challenge plate was removed and added to a new sterile 96-well plate filled with 180 µL TSB. The new 96-well plate was then covered with a regular lid and allowed to incubate for 24 h before MBC values were determined using an automated plate reader to obtain optical density measurements at 600 nm ($OD_{600}$).

Determine the Synergy of Different PKZ18 Analogs and Antibiotic Combinations to Treat Established Staphylococcus Biofilms In Vitro Bacteria growing in a biofilm matrix are intrinsically more resistant to environmental agents and have been shown to tolerate antibiotic concentrations 10- to 1000-fold higher than the corresponding planktonic counterpart. This inherent resistance of bacteria in biofilms and the emergence of antibiotic-resistant bacteria has necessitated the drive to explore competent novel antimicrobial agents such as PKZ18 and the development of combinations of these novel antimicrobial agents with established antibiotics. We determined the minimum biofilm eradication concentration (MBEC) of compounds of Formula I in combination with vancomycin, gentamicin, rifampin, and tetracycline. Three independent experiments were conducted and required a checkerboard dilution to test various concentrations of the following combinations (compound of Formula I+each antibiotic) against S. aureus utilizing an established MBEC™-HTP biofilm model (Innovotech).

Briefly, an overnight culture of S. aureus was diluted to 1×10⁵ cells/mL in cation-adjusted Mueller Hinton broth (MHB) supplemented with 1% human plasma and added to the wells of an MBEC plate. The plate was incubated overnight at 37° C. and shaken at 125 rpm. Following biofilm growth, the lid was then transferred to a standard 96-well plate in which dilutions of PKZ18-22 and the designated antibiotics were prepared individually and in combination in MHB. The treatment plate was incubated for 24 h at 37° C. After incubation, the lid was removed and rinsed in PBS. Following treatment, a tetrazolium (2,3,5-triphenyl tetrazolium chloride, TTC) assay was performed to assess metabolic activity and viability. The lid was rinsed in PBS, transferred to a 96-well plate containing a 0.01% TTC solution in MHB, and incubated at 37° C. overnight. To dissolve the stain from the pegs, the lid was placed in a 96-well plate containing 96% ethanol and the OD of the wells was then read at 490 nm. Data was analyzed with the Bliss independence model using the Combenefit software. The most promising combinations were further investigated with CFU recovery and confocal microscopy analysis.

CFU Recovery

After rinsing in PBS, designated pegs were snapped off the lid using sterile tweezers and placed in 1.5 mL Eppendorf tubes containing 200 µL PBS. Biofilm was disrupted from the pegs by sonicating the tubes for 15 min (Branson M8800H, Branson Ultrasonics, West Chester, Pa., USA), followed by vortexing for 10 s. Three independent serial dilutions were prepared for each sample and plated on tryptic soy agar (TSA) plates that were incubated overnight at 37° C. The plates were then imaged and colonies counted on a ColonyDoc-It™ Imaging station (UVP, Analytik Jena, Beverly, Mass., USA).

Scanning Electron Microscopy

Pegs designated for scanning electron microscopy were snapped off the lid using sterile tweezers and fixed with a 2.5% glutaraldehyde solution (MilliporeSigma, St. Louis, Mo., USA) in 0.2 M sodium cacodylate buffer, pH 7.4 (Electron Microscopy Sciences, Hatfield, Pa., USA) for at least 24 h at 4° C. The pegs were then removed from the fixative and rinsed in cacodylate buffer. The pegs were post-fixed for 1 h with 2% osmium tetroxide (Ted Pella, Inc., Redding, Calif., USA) and then washed again with cacodylate buffer. The pegs were dehydrated in increasing concentrations of ethanol (30%, 50%, 70%, 90%, 100%) and then allowed to air dry overnight. After drying, the pegs were mounted on stubs and sputter coated with gold using a Denton Desk V vacuum sputter system and imaged on a FEI XL30 scanning electron microscope.

Confocal Laser Scanning Imaging

Pegs designated for confocal microscopy were snapped off the lid using sterile tweezers and stained with a SYTO 9/propidium iodide (LIVE/DEAD, BacLight; Invitrogen, Waltham, Mass., USA) solution. The pegs were incubated, covered from the light, for 20 min. After incubation, the pegs were rinsed in PBS and placed on 50 mm glass-bottom dishes (MatTek, Ashland, Mass., USA). The pegs were imaged using a Leica SP5 Inverted Confocal Microscope (Leica Microsystems, Buffalo Grove, Ill., USA) at a resolution of 512×512 pixels using a 63× water immersion objective (63×/1.2W).

Example 1: Pkz18 Binds Specifically to the Specifier Loop

PKZ18 binds with low micromolar dissociation constants to chemically synthesized truncated stem I constructs of the *Bacillus subtilis* glyQS and tyrS T-boxes. Analysis of the UV thermodynamics of two new stem I constructs (not shown) confirmed binding to the stem I specifier loop. PKZ18 thermally destabilized the RNA (change in melting temperature [$\Delta T_m$], −18.52° C.; free energy [$\Delta\Delta G$], +3.41 kcal mol$^{-1}$) when bound to the RNA comprised of the wild-type sequence of the truncated glyQS stem I with the specifier loop. However, PKZ18 did not affect the thermodynamic parameters of a similarly sized construct that has the gly codon but lacks the specifier loop ($\Delta T_m$, −0.33; $\Delta\Delta G$, +0.22) (not shown). This result establishes that PKZ18 binding to stem I occurs within the specifier loop.

Example 2: Compounds of Formula I Have Improved Activity and Bactericidal Effects We compared PKZ18 analogs with variations in chemical structure to better define moieties that contribute to increased efficacy. See Table 1. PKZ18-22 is bactericidal against both *B. subtilis* 168 and MRSA and this activity correlates with a reduced MIC due to the extension of the carbon tail on the benzene para to the thiazole. See Table 2.

TABLE 2

| | Bactericidal effects of compounds | | |
|---|---|---|---|
| PKZ Analog Number | MIC(MBC)$^a$ S. aureus N315 drug in μg/mL | MIC(MBC)$^b$ E. coli drug in μg/mL | T-Box targeting |
| PKZ18-00 | 64 (>256) | >256 (>256) | Yes |
| PKZ18-21 | 64 (>256) | >256 (>256) | Yes |
| PKZ18-22 | 32 (64) | >256 (>256) | Yes |
| PKZ18-52 | 32 (64) | >256 (>256) | Yes |
| PKZ18-53 | 32 (64) | >256 (>256) | Yes |
| PKZ18-54 | 128 (256) | >256 (>256) | No |
| PKZ18-55 | >256 (>256) | >256 (>256) | No |
| PKZ18-56 | >256 (>256) | >256 (>256) | No |

TABLE 2-continued

| | Bactericidal effects of compounds | | |
|---|---|---|---|
| PKZ Analog Number | MIC(MBC)$^a$ S. aureus N315 drug in μg/mL | MIC(MBC)$^b$ E. coli drug in μg/mL | T-Box targeting |
| PKZ18-57 | >256 (>256) | >256 (>256) | No |
| PKZ18-58 | NT (NT) | NT (NT) | No | a=Drug concentrations are represented in micrograms per milliliter against *S. aureus* N315 and *E. coli*. b=Gram-negative control-showing drugs do not target an organism that does not contain T-boxes. c=Confirmation of inhibition of T-box mechanism from qRT-PCR assay. Different chemical moieties are listed corresponding to the three locations where changes to the compound identified in Table I as PKZ18-00 (also referred to herein as PKZ18) were made. The MIC and MBC against the Gram-positive MRSA, as well as the Gram-negative *E. coli*, are shown. PKZ18-52 and PKZ18-53 have a norbornene moiety instead of norbornane.

The reduced MIC, however, was lost by changing the bridge C7 of the norbornane to an oxygen. Comparison of PKZ18-54 with PKZ18-57 suggests that a straight aliphatic chain para to the thiazole enhances activity (PKZ18-54) compared to that of a branched chain (PKZ18-57). Increasing the polarity, as with the ether in PKZ18-55, nullified activity. The substitution of norbornene for the norbornane maintained the bioactivity, making further derivatizations possible by way of additions to the double bond. The methyl group at position 5 of the thiazole, or the absence thereof, had no effect on activity, as shown by MIC and minimal bactericidal concentration (MBC) values with PKZ18-22 and PKZ18-53.

PKZ18 is active against *B. subtilis* 1A5 grown in minimal media at much lower concentrations than the reported MIC. In contrast, media-dependent antimicrobial activity against *Escherichia coli* has been reported by others where the antibiotic loses efficacy in nutrient-limiting conditions. To measure the effect of growth media on activity, we compared the MIC of parent PKZ18 against both *B. subtilis* 168 and *S. aureus* 4220 in rich versus minimal media. The MICs of PKZ18 were 8-(*B. subtilis* 168) and 4-fold (*S. aureus* 4220) lower when the cultures were grown in minimal versus rich media. Similarly, PKZ18-22 exhibited a 4-fold reduction in MIC, while PKZ18-52 and PKZ18-53 had 2-fold reductions against the MRSA strain *S. aureus* N315 in minimal compared to rich media. See Table 3. In contrast, gentamicin and mupirocin had increased MICs in minimal media compared to rich media against *S. aureus* N315.

TABLE 3

| | Media-dependent activity of drugs$^d$ | | | |
|---|---|---|---|---|
| | MIC (μg/ml) against B. subtilis 168 in: | | MIC (μg/ml) against S. aureus in: | |
| Drug | Rich media | Minimal media | Rich media | Minimal media |
| PKZ18 | 64 | 8 | 64$^a$ | 16$^a$ |
| PKZ18-22 | 16 | 4 | 32$^b$ | 8$^b$ |
| PKZ18-52 | NT$^c$ | NT | 16-32$^b$ | 16$^b$ |
| PKZ18-53 | NT | NT | 32$^b$ | 16$^b$ |

TABLE 3-continued

| | Media-dependent activity of drugs[d] | | | |
|---|---|---|---|---|
| | MIC (μg/ml) against B. subtilis 168 in: | | MIC (μg/ml) against S. aureus in: | |
| Drug | Rich media | Minimal media | Rich media | Minimal media |
| Gentamicin | 0.125 | 0.25 | 0.5[b] | 2.0[b] |
| Mupirocin | NT | NT | 0.25[b] | 1.0[b] |

[a] = S. aureus 4220.
[b] = S. aureus N315.
[c] = NT, not tested;
[d] = PKZ18 analogs are more effective in minimal media against both B. subtilis and S. aureus, whereas gentamicin and mupirocin are more effective in rich media.

Example 3: Broad T-Box Targeting By Compounds Of Formula I

Figure 2A:
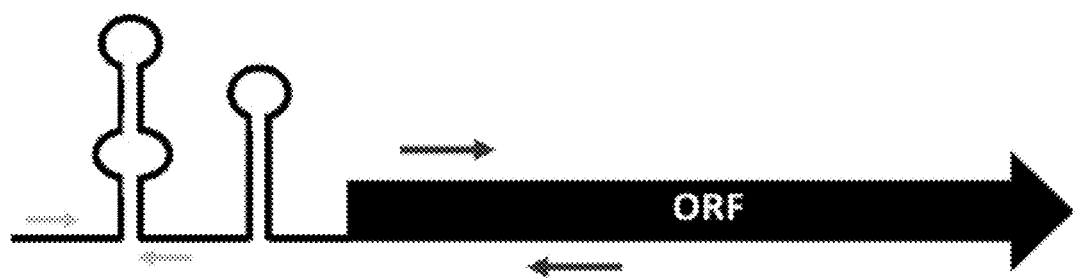
FIGS. 2A-2D show a PKZ18 analog's effect on transcriptional read-through in minimal media in accordance with aspects of the present disclosure.
Figure 2B:
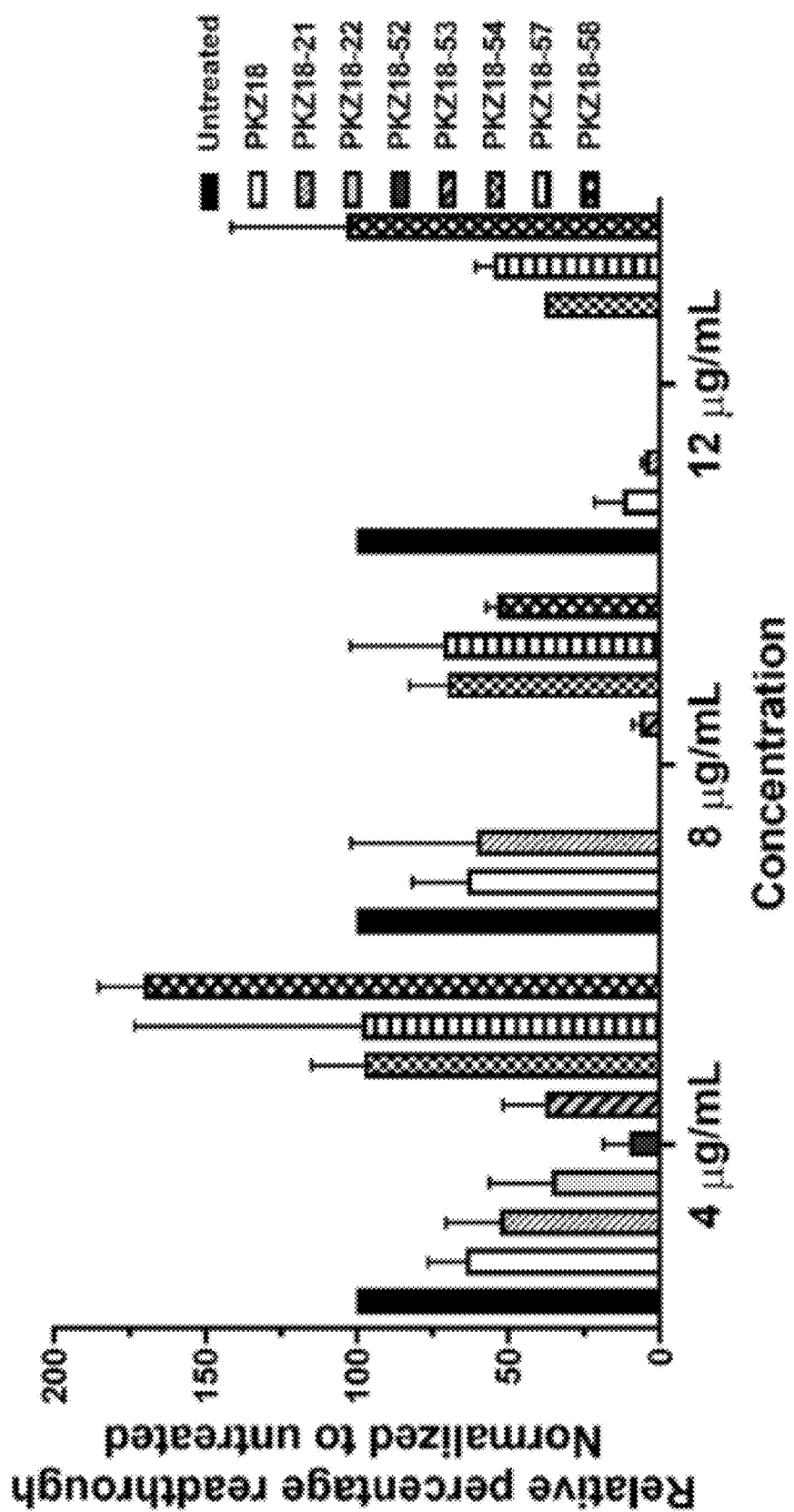
Figure 2C:
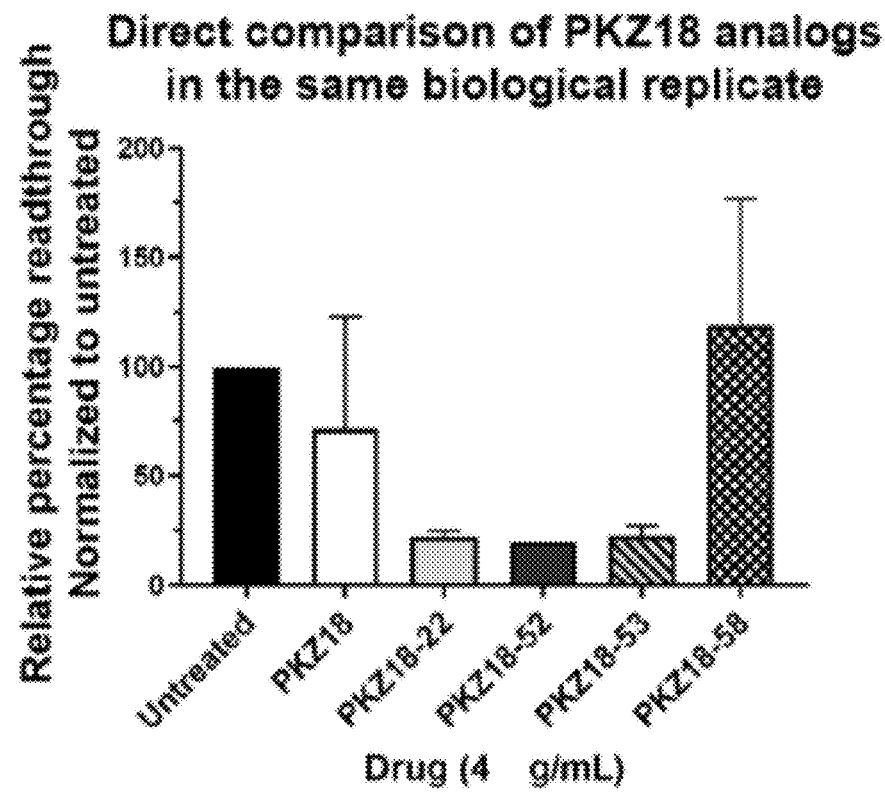

PKZ18-21, PKZ18-22, PKZ18-52, and PKZ18-53 inhibited T-box-controlled expression of glyQS in the glycine auxotroph B. subtilis 1A5, with increasing concentrations showing increased termination of read-through by reverse transcription-quantitative PCR (qRT-PCR). FIGS. 2A and 2B. Additionally, PKZ18-22, PKZ18-52, and PKZ18-53 inhibited B. subtilis 1A5 read-through significantly better than PKZ18 (at 4 μg/ml of each drug) when the bacteria were grown side by side in the same biological replicate assay. FIG. 2C. These compounds of Formula I inhibited culture growth, and no RNA could be obtained at 12 μg/ml where PKZ18 was previously shown to be most active.

Figure 3A:
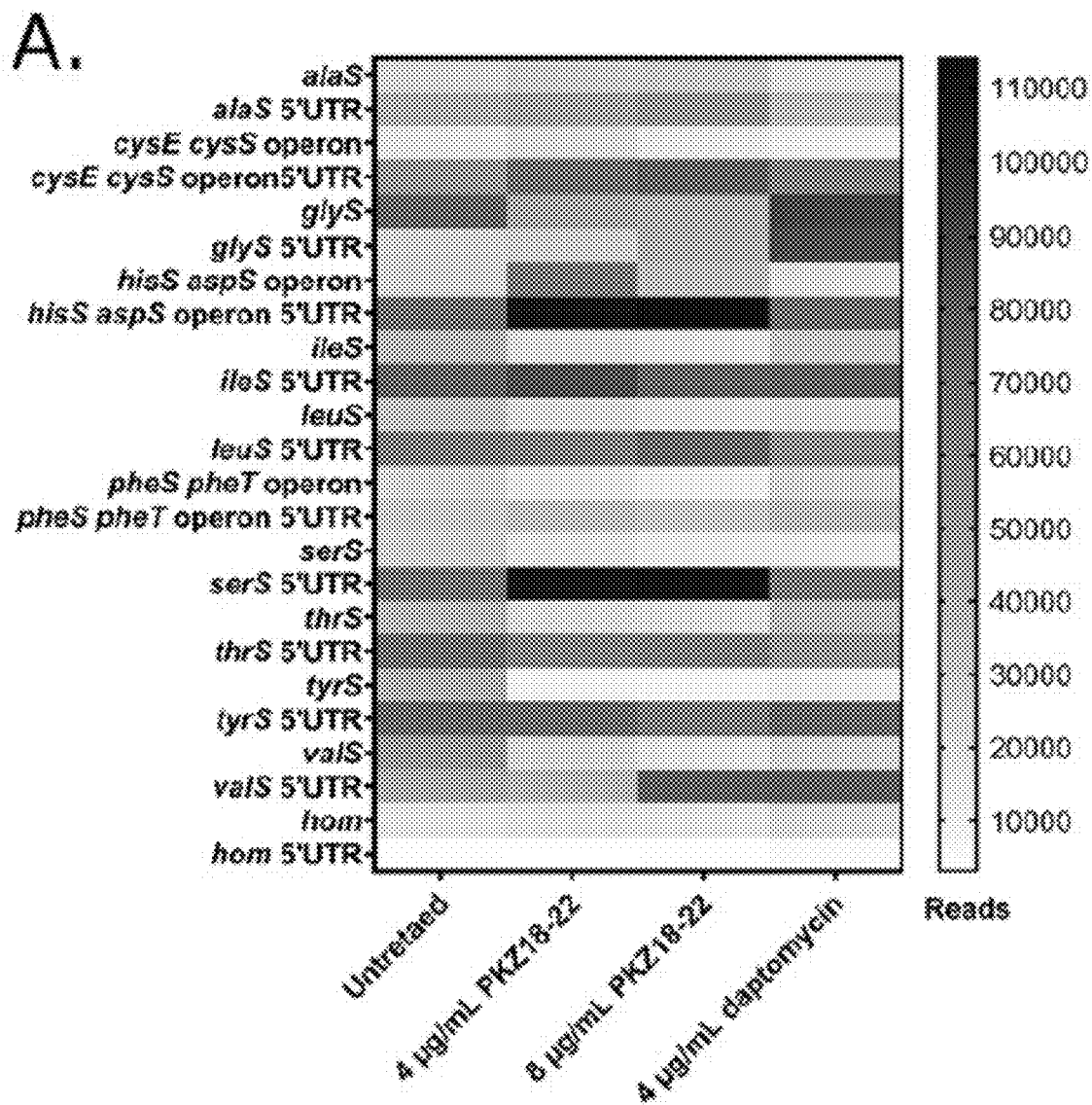
FIGS. 3A-3F show RNA sequencing of MRSA showing the mean of two biological replicates grown in minimal media in accordance with aspects of the present disclosure.
Figure 3B:
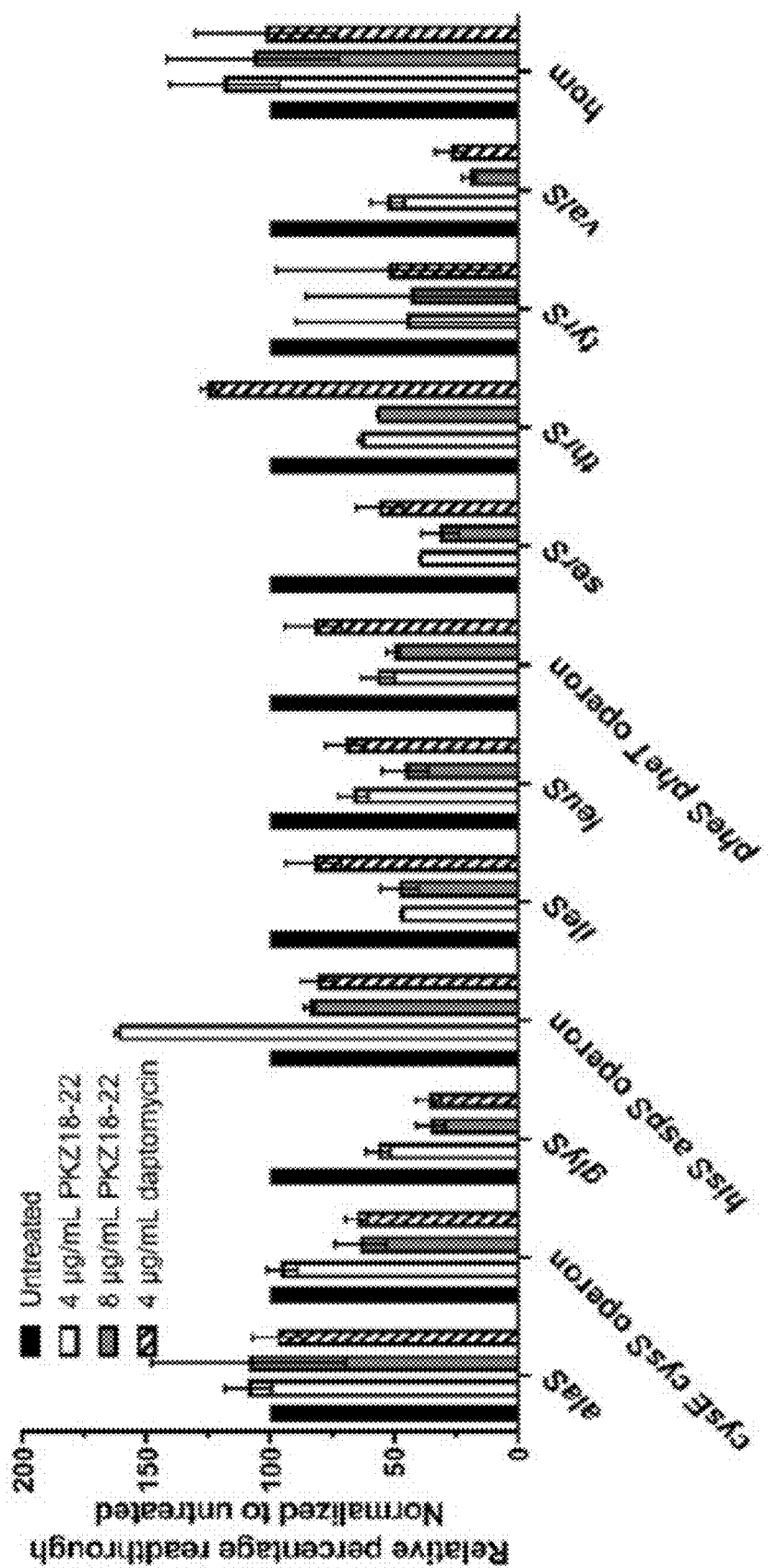

RNA sequencing was used to determine if native expression of T-box-controlled genes was affected by PKZ18-22 in MRSA. We compared the expression of the 5'UTR of T-box-regulated genes to the expression of their open reading frames (ORFs). The expression of 8 out of the 12 genes under T-box control was reduced, one remained at untreated levels when tested at 8 μg/ml PKZ18-22, and three remained at untreated levels with either 4 or 8 μg/ml PKZ18-22 (FIG. 3A), indicating an inhibitory effect by PKZ18-22 on the T-box-regulated genes with decreased expression. Elevated 5'-UTR expression for several T-box-mediated genes following PKZ18-22 treatment further indicated an increase in transcriptional initiation with early termination in the presence of PKZ18-22 (FIG. 3A). We then ratioed the reads from the ORF to the read numbers in the 5'UTR for each gene to represent relative read-through and normalized the data to the untreated control. There was a reduction in read-throughs of glyS (P=0.004311), ileS (P=0.010565), leuS (P=0.013825), pheST (P=0.001594), serS (P=0.005975), thrS (P=0.000019), and valS (P=0.000566), indicating inhibition of these T-boxes by both concentrations of PKZ18-22; the P values shown in parentheses after each gene are for 8 μg/ml treatment based on a t test comparing the read-through to the untreated sample (FIG. 3B). These were also all significant hits for the 8-μg/ml PKZ18-22 treatment (not shown). Expression and read-through of tyrS was reduced, but the read-through reduction was not statistically significant (FIGS. 3A-3B). The cysteine and histidine T-boxes (cysE-cysS and hisS-aspS operons, respectively) were inhibited only by the higher concentration of PKZ18-22. Read-through of alaS was not inhibited, but 8 μg/ml of PKZ18-22 was sufficient to maintain expression at the same level as 4 μg/ml in spite of increased transcription initiation (FIGS. 3A-3B). The only T-box-regulated gene in MRSA that does not transcribe an aaRS gene, hom, is preceded by a methionine T-box and was expressed at counts too low to allow conclusions. We used 4 μg/ml of daptomycin as a control antibiotic. It did not significantly affect initiation of T-box-controlled genes, but expression and read-through with daptomycin were lower than untreated for many of the genes (FIGS. 3A-3B).

Figure 3C:
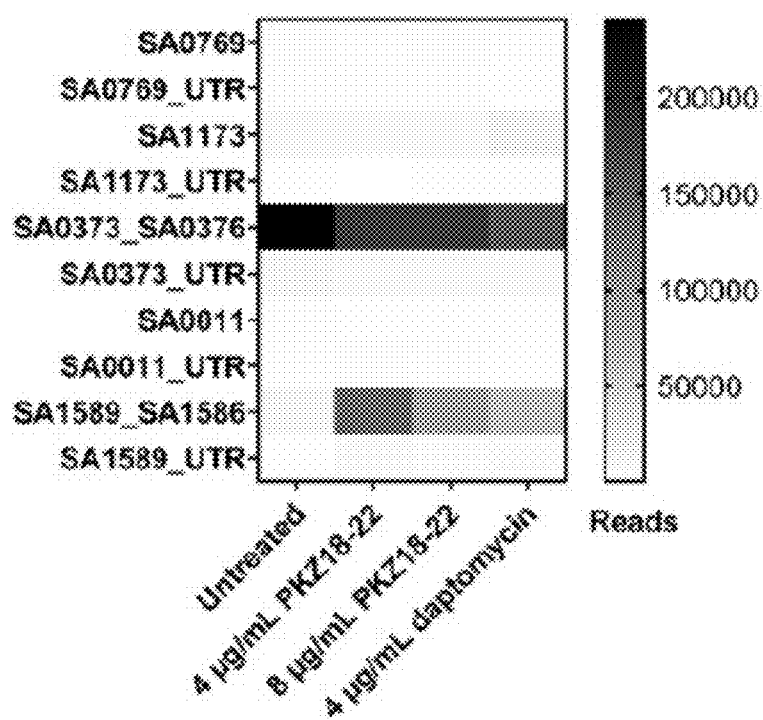
Figure 3D:
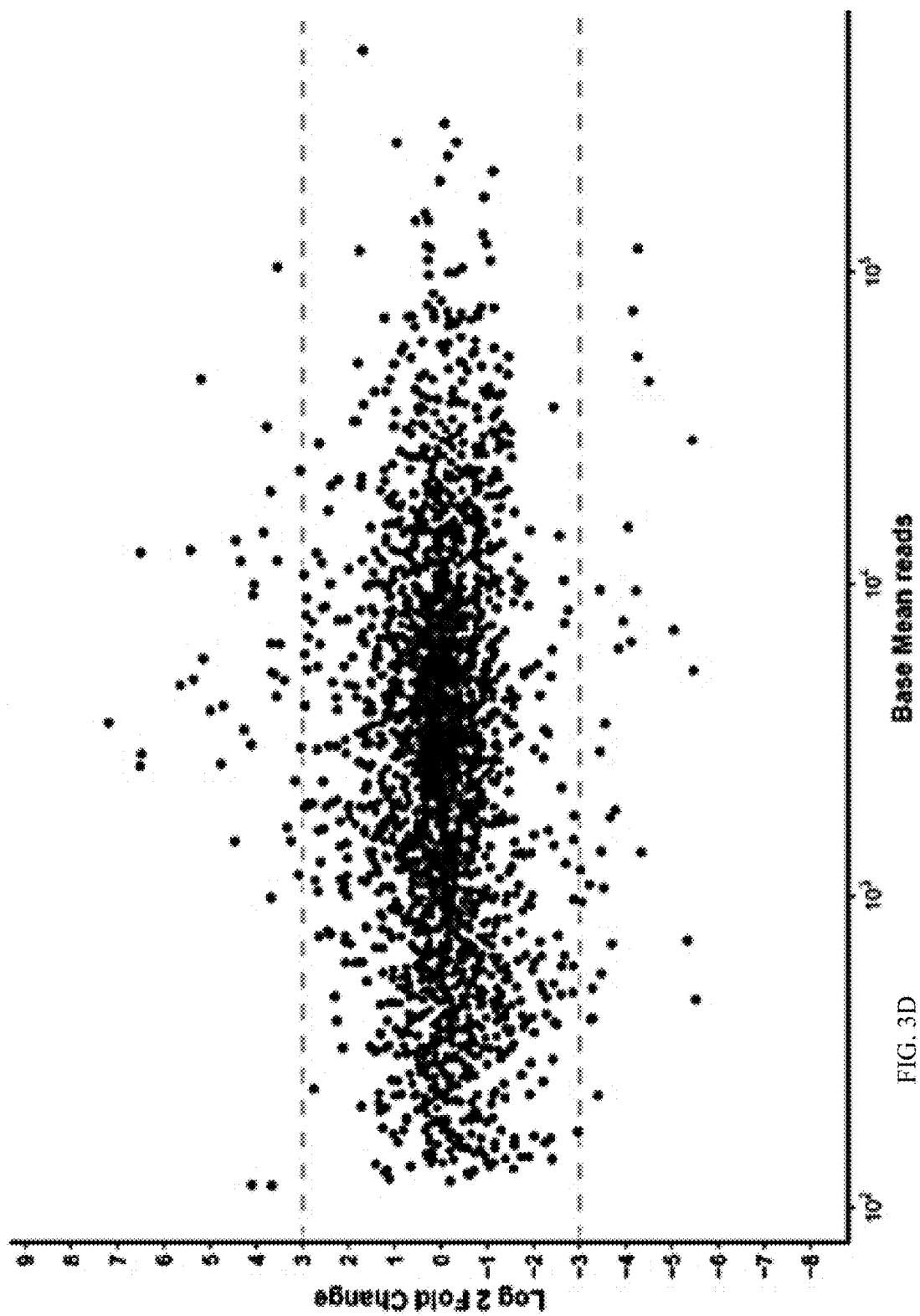
Figure 3E:
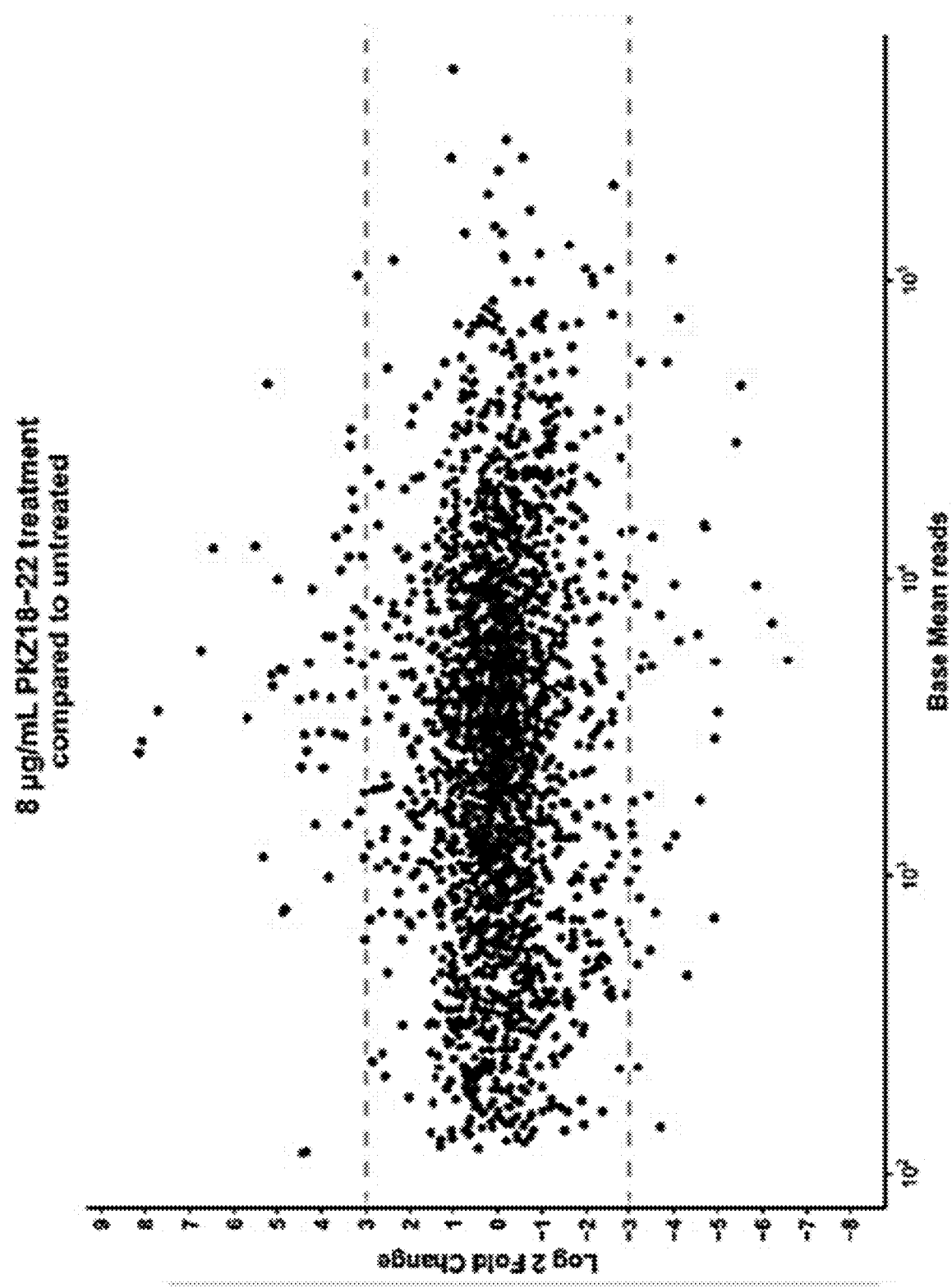
Figure 3F:
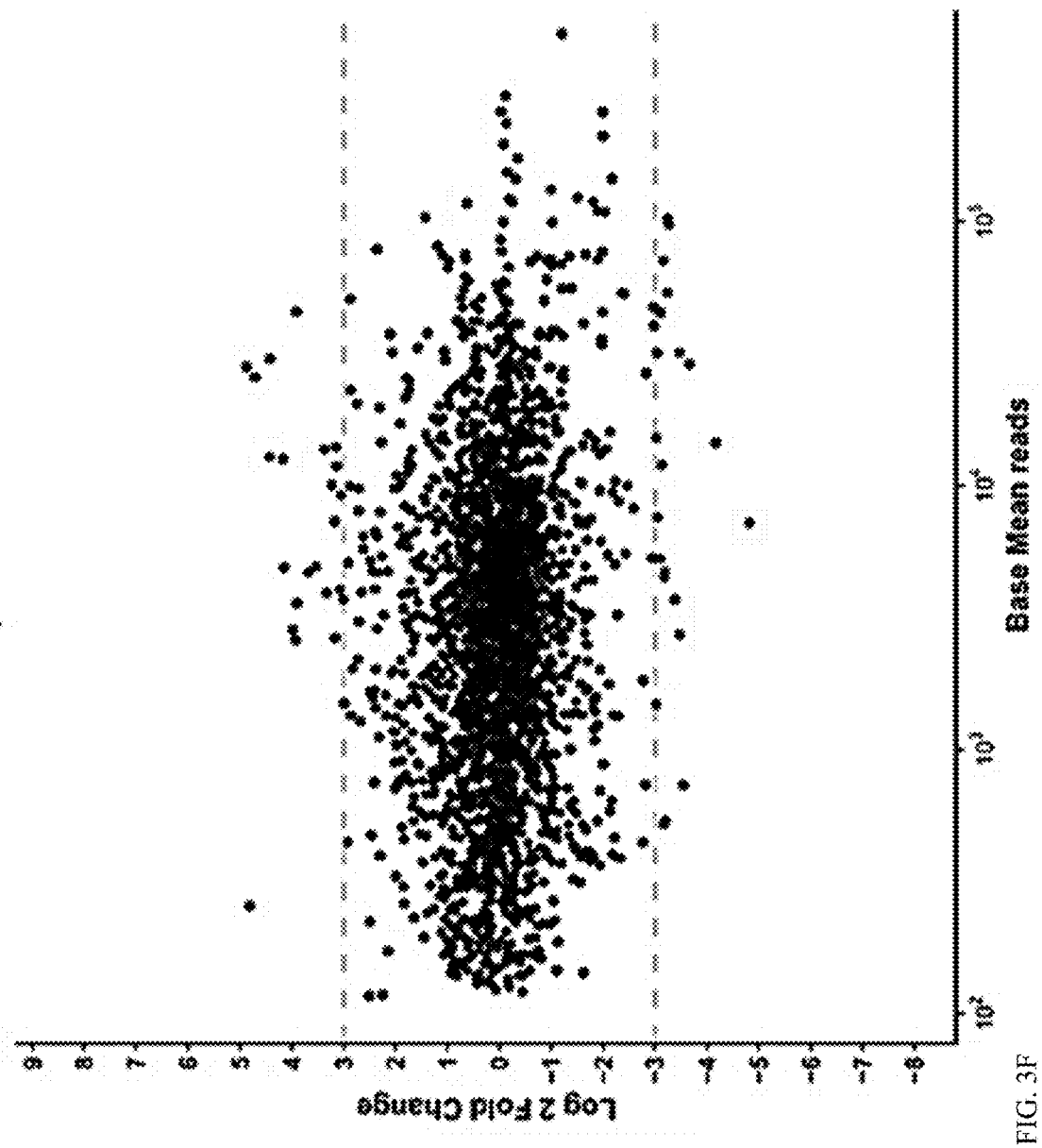

At least 40 genes or operons are controlled by riboswitches or riboswitch-like RNA elements in S. aureus. We confirmed the T-box-specific activity of PKZ18-22 by comparing the 5'UTR expression and ORF expression of other riboswitch-controlled genes. No clear trends with PKZ18-22 treatment were evident, and relative read-through of the tested genes did not significantly change with treatment (FIG. 3C). Treatment was expected to cause a large depletion of aminoacylated tRNAs with the possibility of pleiotropic changes in native gene expression as a stress reaction. Treatment with PKZ18-22 resulted in a large overall change in expression, which was similar to that associated with daptomycin (FIGS. 3D-3F). Volcano plots of the three treatments also indicate a large pleiotropic effect by all treatments (not shown).

Figure 2D:
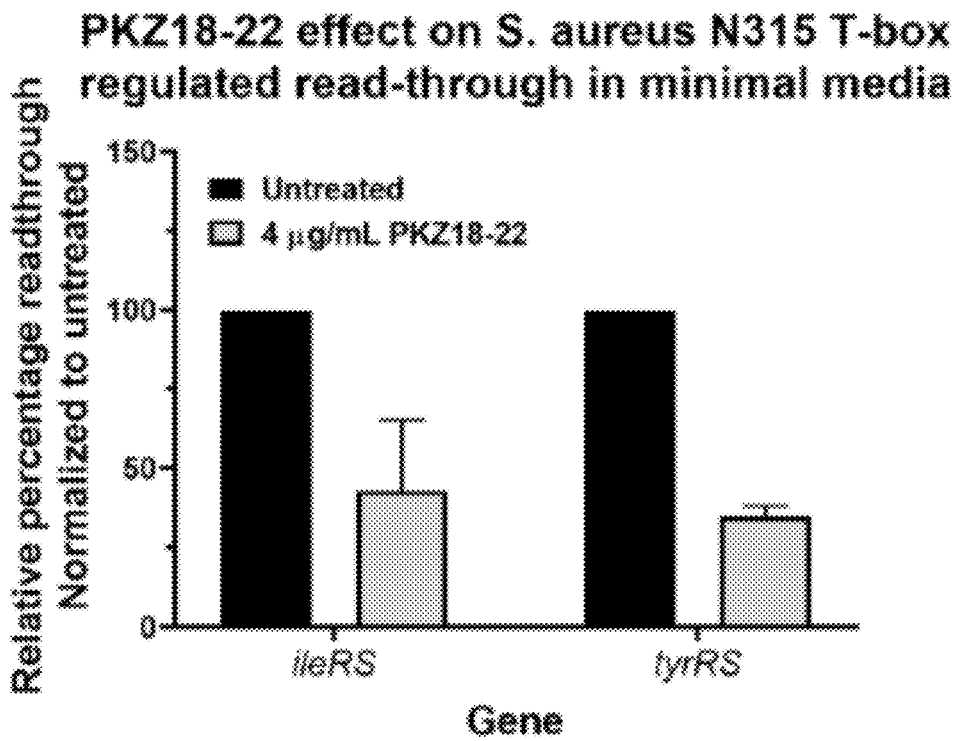

Comparison of the relative read-through of ileS and tyrS in MRSA grown in minimal media showed that PKZ18-22 at 4 μg/ml caused a decrease in the read-through of both genes, consistent with PKZ18-22 working as an inhibitor of the T-box mechanism (FIG. 2D). A similar but less pronounced trend was observed when MRSA was grown in rich media and treated with 8 μg/ml of PKZ18-22. The read-through of both ileS and tyrS was reduced compared to that in untreated MRSA (not shown). However, expression of the genes is reduced in nutrient-rich conditions, as the pool of uncharged tRNAs tends to be relatively low as well.

Example 4: Synergistic Activity of Compounds of Formula I with Different Antibiotics PKZ18-22 was synergistic with neomycin B and with kanamycin A (fractional inhibitory concentration [FIC], 0.38), and PKZ18-22, PKZ18-52, and PKZ18-53 were all synergistic with gentamicin (FIC, 0.38) (FIG. 4). However, interaction between streptomycin and PKZ18-22 was only additive (FIC, 0.75). Additionally, both the beta-lactam antibiotic ampicillin and the ribosome-targeting chloramphenicol showed additive effects with PKZ18-22 and PKZ18-53 (FIC, 0.75). No combinatorial effects were observed with PKZ18 analogs and the other drugs tested, including some antibiotics commonly used to treat MRSA, namely, mupirocin, vancomycin, oxacillin, and daptomycin. No antagonistic interactions with PKZ18 analogs were discovered.

Synergy observed between PKZ18-22 and gentamicin was substantial, with a 4-fold decrease in the MIC of PKZ18-22 and an 8-fold decrease in the MIC of gentamicin. Similar effects were observed for the combinations of PKZ18-22 with neomycin or with kanamycin, PKZ18-52 with gentamicin, and PKZ18-53 with gentamicin. Due to limited supply of the novel analogs, not all combinations were tested with all the analogs; however, the analogs used replicated the effect PKZ18-22 had on the MICS of the drugs with which they were tested.

Example 5: Cytotoxicity

Figure 5A:
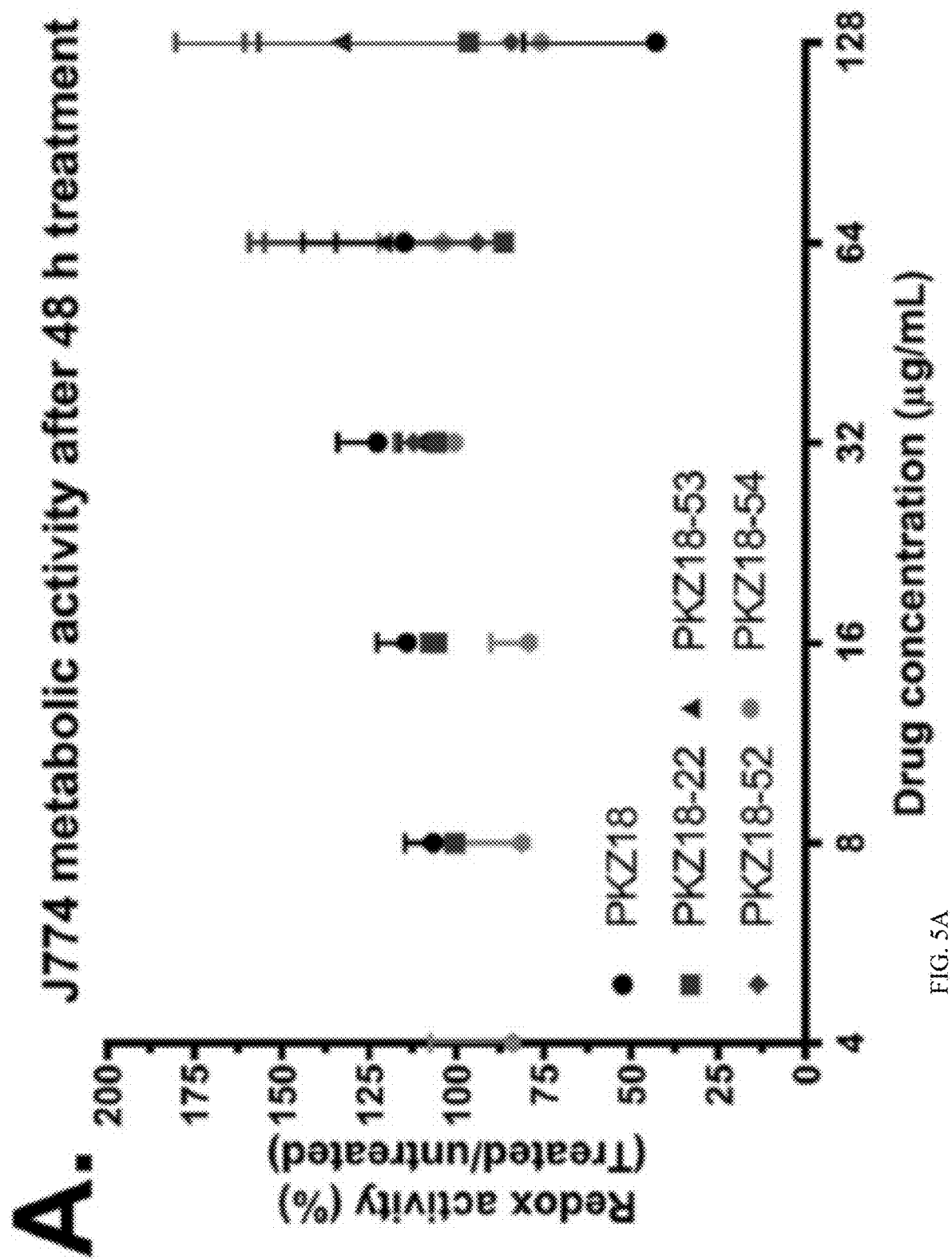
FIGS. 5A-5D show cytotoxicity of PKZ18 analogs in accordance with aspects of the present disclosure. All values are normalized to an untreated sample. A drug concentration of 0 corresponds to the DMSO control used in each experiment.
Figure 5B:
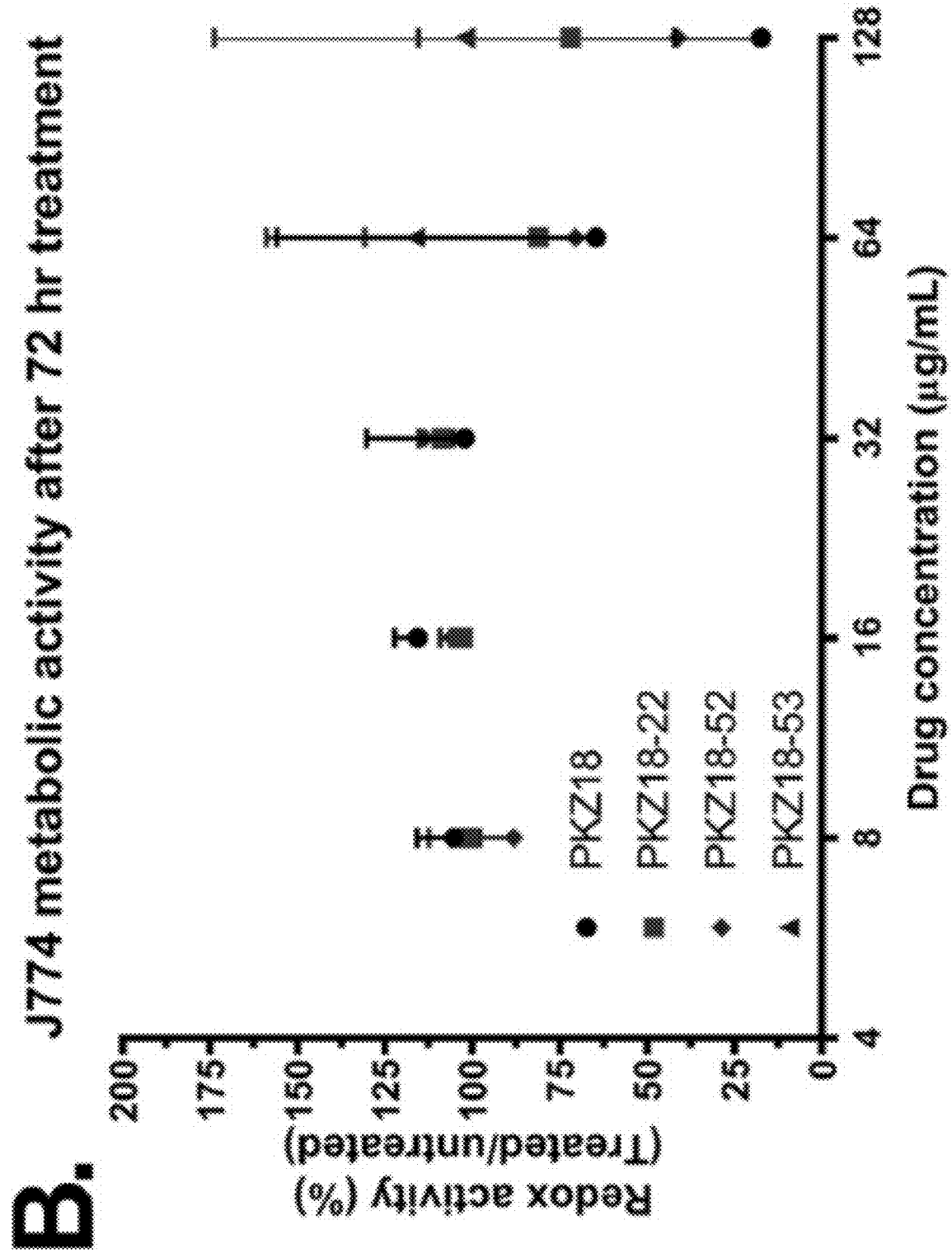
Figure 5C:
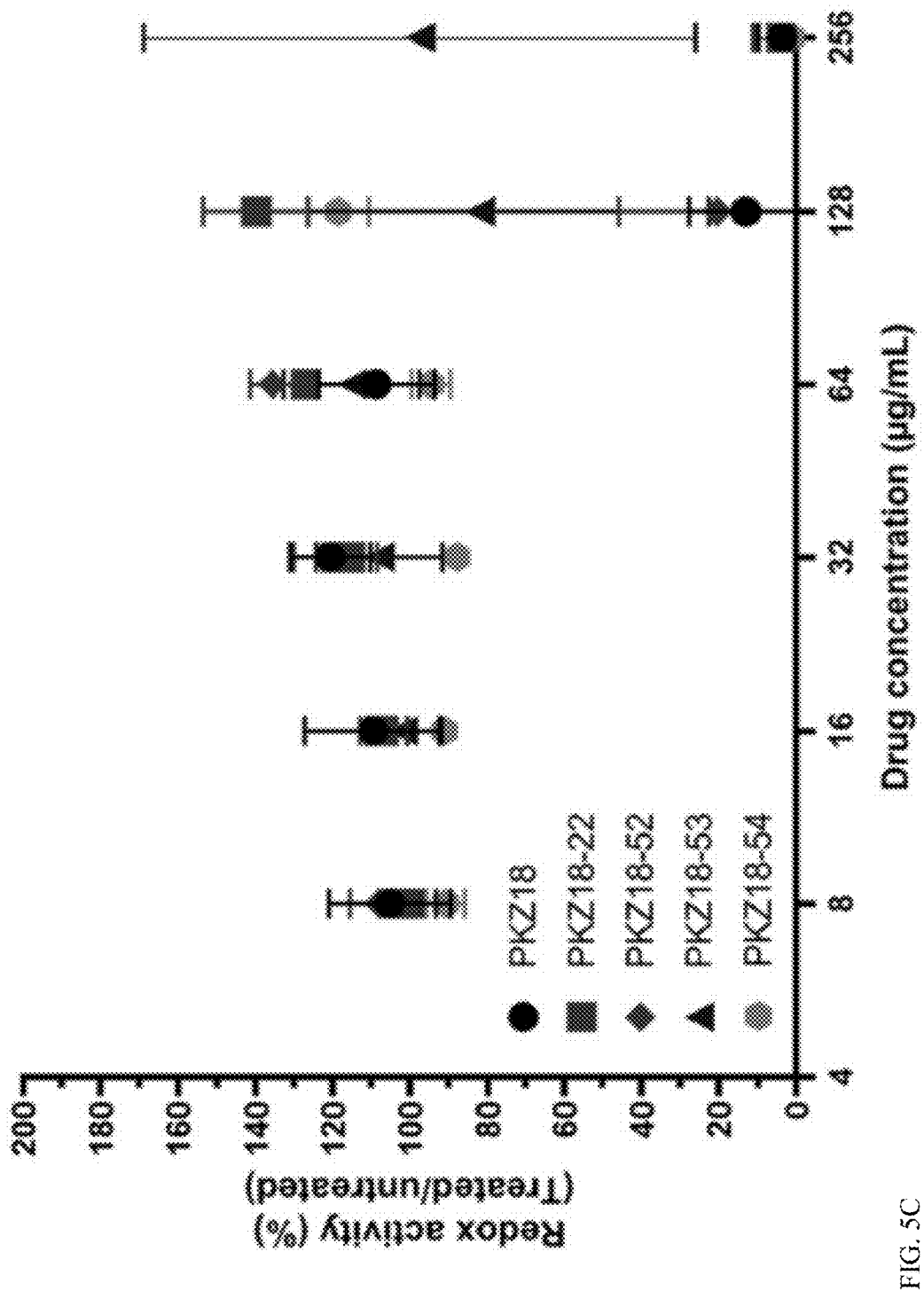

Compounds of Formula I were tested for cytotoxicity against A549 human lung epithelial cells as well as against J774.16 murine macrophages by measuring both the redox potential of alamarBlue as an indicator of metabolic function and trypan blue staining for cell viability. After 48 hours of treatment, PKZ18 increased cellular redox activity at 64 µg/ml but decreased after 72 hours (FIGS. 5A-5B) and PKZ18 caused a near-total reduction of redox activity at 128 µg/ml after 48 hours (FIGS. 5A-5C), i.e., cytotoxicity at 2-fold above the MIC. Other analogs showed increased redox activity at 128 µg/ml and a complete loss of redox activity at 256 µg/ml, indicative of stress and killing, respectively (FIG. 5C). The data are consistent between the two cell lines tested, although we were not able to test J774.16 cells at 256 µg/ml due to their low tolerance to dimethyl sulfoxide (DMSO) (FIGS. 5A and 5B). The data from the alamarBlue assay indicated lower cytotoxicity of the analogs than compound PKZ18, where PKZ18 showed cytotoxicity at the MIC, and the analogs were 2- to 4-fold above the MIC.

Figure 5D:
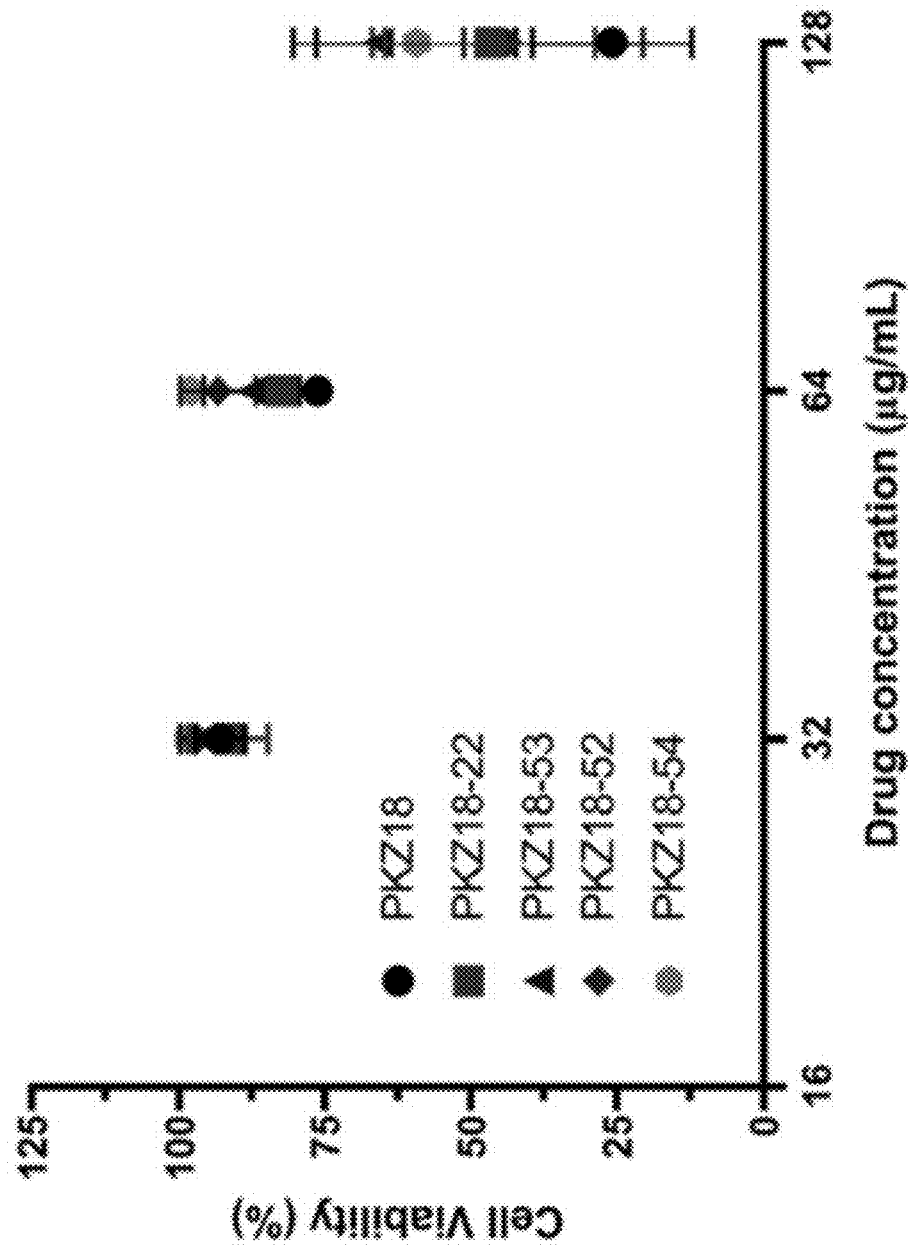

Cell viability measured by trypan blue cell staining of the macrophages showed that the cells retained a 76% viability with PKZ18 at 64 µ/ml, while there was 82 to 98% cell viability with PKZ18-22, PKZ18-52, PKZ18-53, and PKZ18-54. Macrophage viability was only 25% after treating with 128 µg/ml PKZ18 for 48 hours, but it was 43 to 65% with the other analogs. FIG. 5D.

Synergistic concentrations at which the PKZ18 analogs were effective with the aminoglycosides, as well as ampicillin and chloramphenicol, showed no change in metabolic activity of A549 cells, indicating that the combinatorial concentrations required for inhibiting bacterial growth are nontoxic to human lung epithelial cells (not shown)

Example 6: Mutation Frequency of Pkz18-22 and Characterization of Resistant Mutant To measure resistance, we tested PKZ18-22 or gentamicin against MRSA and used *B. subtilis* as a control. MRSA exposed to MBC levels (64 µg/ml) of PKZ18-22 did not readily form resistant colonies, with only one colony recovered from a total of $1.8 \times 10^{11}$ CFU plated, giving a resistance frequency of $5.6 \times 10^{-12}$. In comparison, MRSA plated on 10 µg/ml gentamicin (20× MIC and 5× MBC against MRSA) showed a resistance frequency of $1.6 \times 10^{-7}$. This clearly demonstrates that PKZ18-22 is highly refractory to resistance, consistent with the RNA sequencing results that PKZ18-22 targets multiple T-boxes simultaneously. No PKZ18-resistant colonies were found. Additionally, *B. subtilis* did not generate resistant colonies against either PKZ18 or PKZ18-22. The mutant emerging from the fluctuation assay (named PKZRSA1) was sequenced for the tyrosine T-box, but no mutations were found. We confirmed the mutant was resistant with a kill curve assay where the mutant, but not the wild type (WT), grew through in the presence of PKZ18-22 (not shown). The levels of live cells compared to optical density (OD) remained constant with 64 µg/ml of PKZ18-22 and slightly decreased with 128 µg/ml, but both concentrations caused the number of live WT MRSA relative to optical density to decrease (not shown), indicating a truly resistant mutant. We used an ethidium bromide fluorescence-based assay to measure efflux and influx to determine if PKZRSA1 had altered influx or efflux activity. No differences in either efflux or influx were observed, so this is unlikely to be the cause for resistance.

PKZRSA1 showed a 2-fold increase in the MIC against all PKZ18 analogs tested and also exhibited a 2-fold increase in MIC against gentamicin. We screened PKZRSA1 against a wide variety of antibacterial compounds to see if it was more resistant against other drugs. The MICs of the aminoglycosides rose 2- or 4-fold against the mutant compared to the WT, and the MICs of the cell wall-targeting antibiotics vancomycin and oxacillin also increased. Vancomycin had a 2-fold increase in its MIC against the mutant, whereas 16 times more oxacillin was needed to inhibit the growth of PKZ18-22-resistant MRSA than WT MRSA. Mupirocin, tetracycline, daptomycin, and rifampin, however, showed no change in the MIC between WT and PKZRSA1. Surprisingly, the MIC of chloramphenicol was 2-fold lower for PKZRSA1 than the WT MRSA (FIG. 6). The media-dependent activity of antibiotics was not tested against PKZRSA1; however, the FIC of PKZ18-22 and gentamicin was 0.38 in both rich and minimal media against WT MRSA (data not shown).

Example 7: Biofilm Growth is Retarded by Compounds of Formula I

Figure 7A:
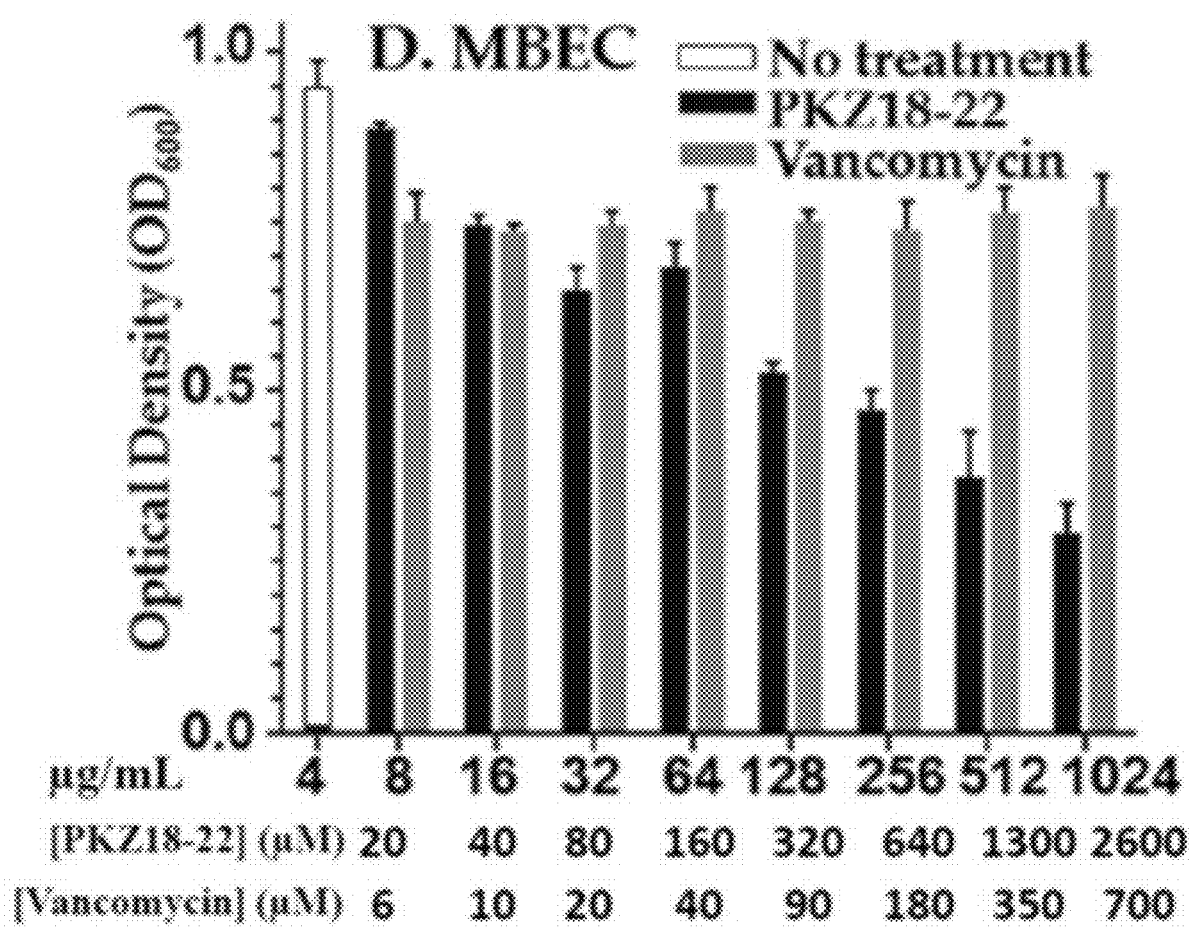
FIGS. 7A-7C show assessment of PKZ18-22 effect on *Staphylococcus* biofilms in accordance with aspects of the present disclosure.
Figure 7B:
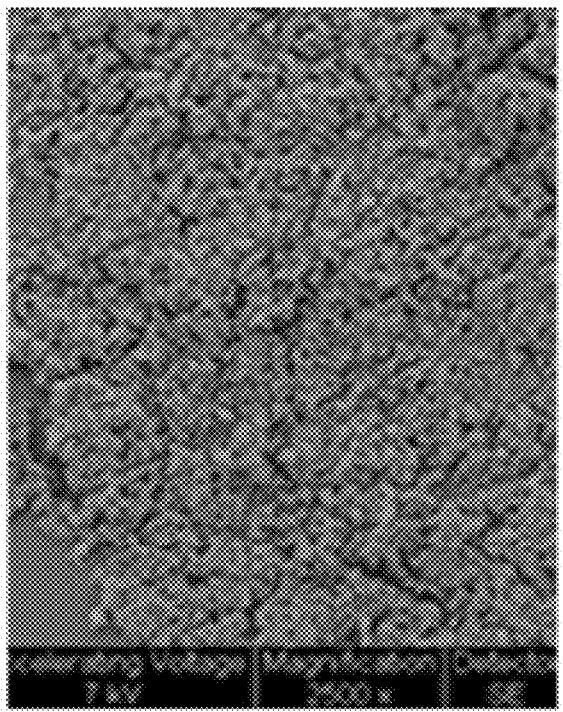
Figure 7C:

PKZ18-22 activity against known biofilm-producing methicillin-resistant Staphylococcus aureus (MRSA) was evaluated using an established MBEC™-HTP biofilm model (Innovotech) for studies of implant-associated infections. PKZ18-22 (256 µg/mL) demonstrated improved potency when compared to vancomycin (1024 µg/mL) at a similar molar concentration. Vancomycin has long been considered an antibiotic of last resort against Gram-positive antibiotic-resistant bacteria and has been shown to be most valuable in treating PJIs. It is a glycopeptide and hinders bacterial growth by inhibiting peptidoglycan cross linkage during bacterial cell wall synthesis. Resistance emerges by the bacterium substituting an amino acid in a cell-wall component, preventing vancomycin from binding. The mean recovery growth of the PKZ18-22-treated *S. aureus* was 4.3 $\log_{1_-}$ CFU/mL versus 5.2 $\log_{10}$ CFU/mL for the vancomycin-treated pegs on which the biofilms were grown (p=0.01; FIG. 7A). This corresponded to a 2.5 log reduction in CFU/mL for the PKZ18-22-treated biofilms compared to 1.6 for the vancomycin-treated samples. We compared the minimum biofilm eradication concentrations (MBEC) efficacy over a range of concentrations for PKZ18-22 and vancomycin against Staphylococcus biofilms (same parameters as FIG. 2C: inoculum, media concentration, etc., except plates read at 600 instead of 625) (FIG. 7A). A 1.024 mg/mL concentration of vancomycin is a concentration of approximately 0.7 mM. A concentration of 1.024 mg/mL of PKZ18-22 is approximately 2.6 mM. A concentration of 256 µg/mL of PKZ18-22 is similar to a 1024 µg/mL concentration of vancomycin. The highest concentration of vancomycin was not effective. We checked the efficacy over a range of concentrations for PKZ18-22 and vancomycin against planktonic growth of Staphylococcus. There was no growth with vancomycin; PKZ18-22 exhibited a killing curve. Using scanning electron microscopy, we saw that the PKZ18 treated biofilms differed in cell morphology, thickness, and population density compared with the untreated biofilms (FIG. 7B, 7C).

Example 8: Synergistic Activity of Pkz18-22 with Other Antibiotics

Figure 8:
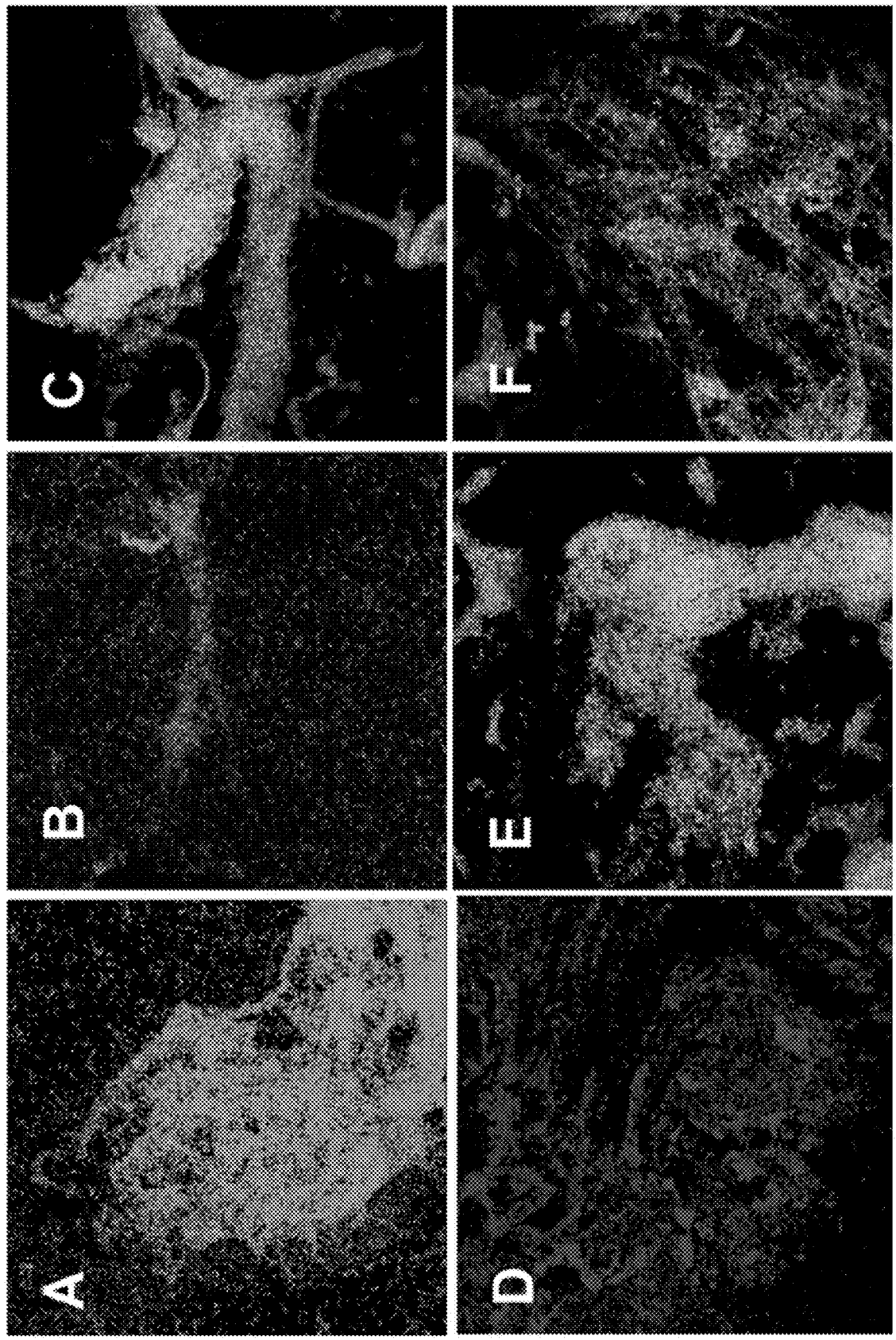
FIG. 8 shows PKZ18-22—antibiotic synergy on *S. aureus* biofilm growth in accordance with aspects of the present disclosure. Top left: Biofilm grown for 24 h with no treatment. Top middle: Biofilm growth after 24 h exposure to 25 µg/mL PKZ18-22. Top right: Growth after 24 h exposure to 4 µg/mL gentamicin. Bottom left: Growth after 24 h exposure to 64 µg/mL gentamicin+25 µg/mL PKZ18-22. Bottom middle: Growth after 24 h exposure to 4 µg/mL vancomycin. Bottom right: Growth of *S. aureus* after 24 h exposure to 4 µg/mL vancomycin+25 µg/mL PKZ18-22.
Figure 10:
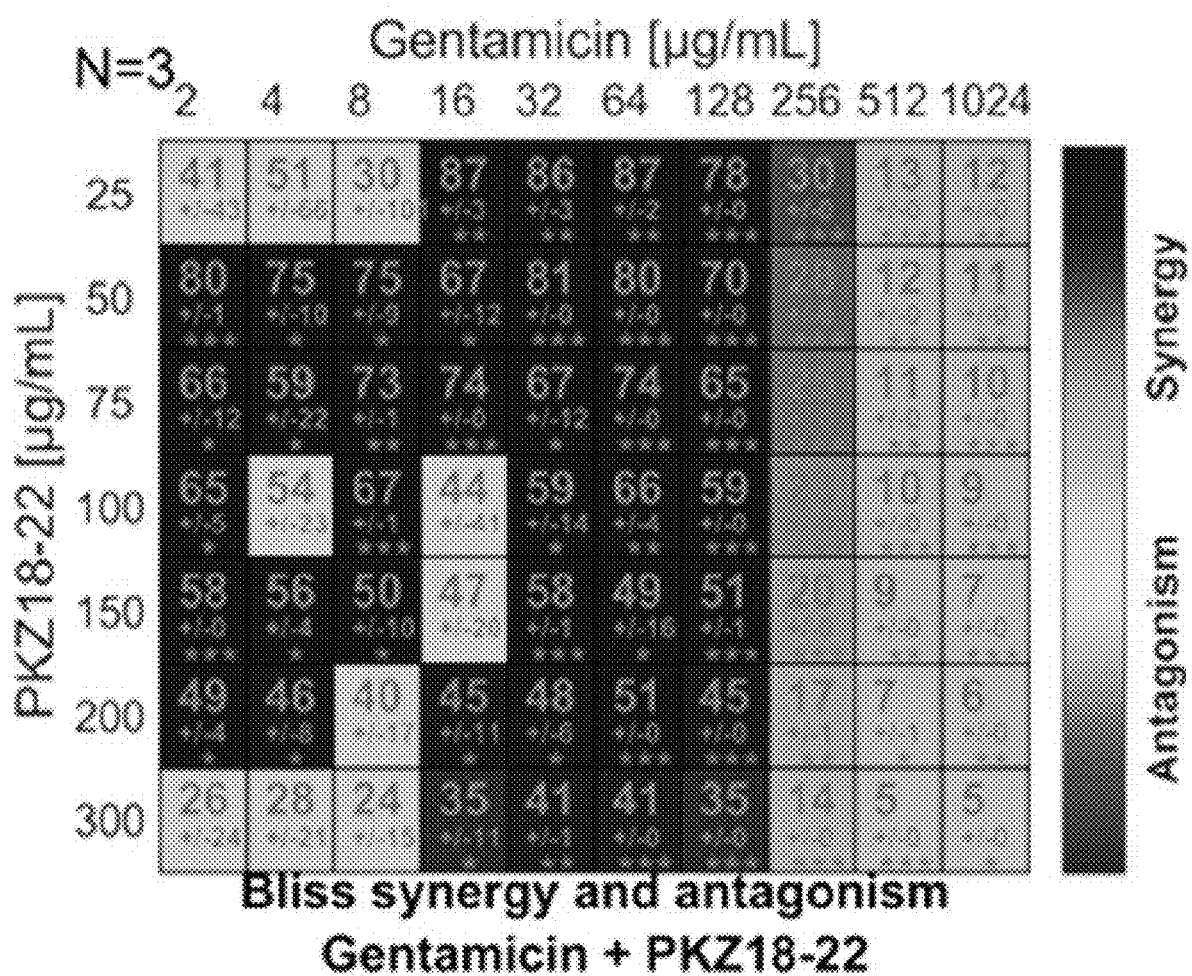
FIGS. 10, 11, and 12 show synergy matrix scores in accordance with aspects of the present disclosure.
Figure 11:
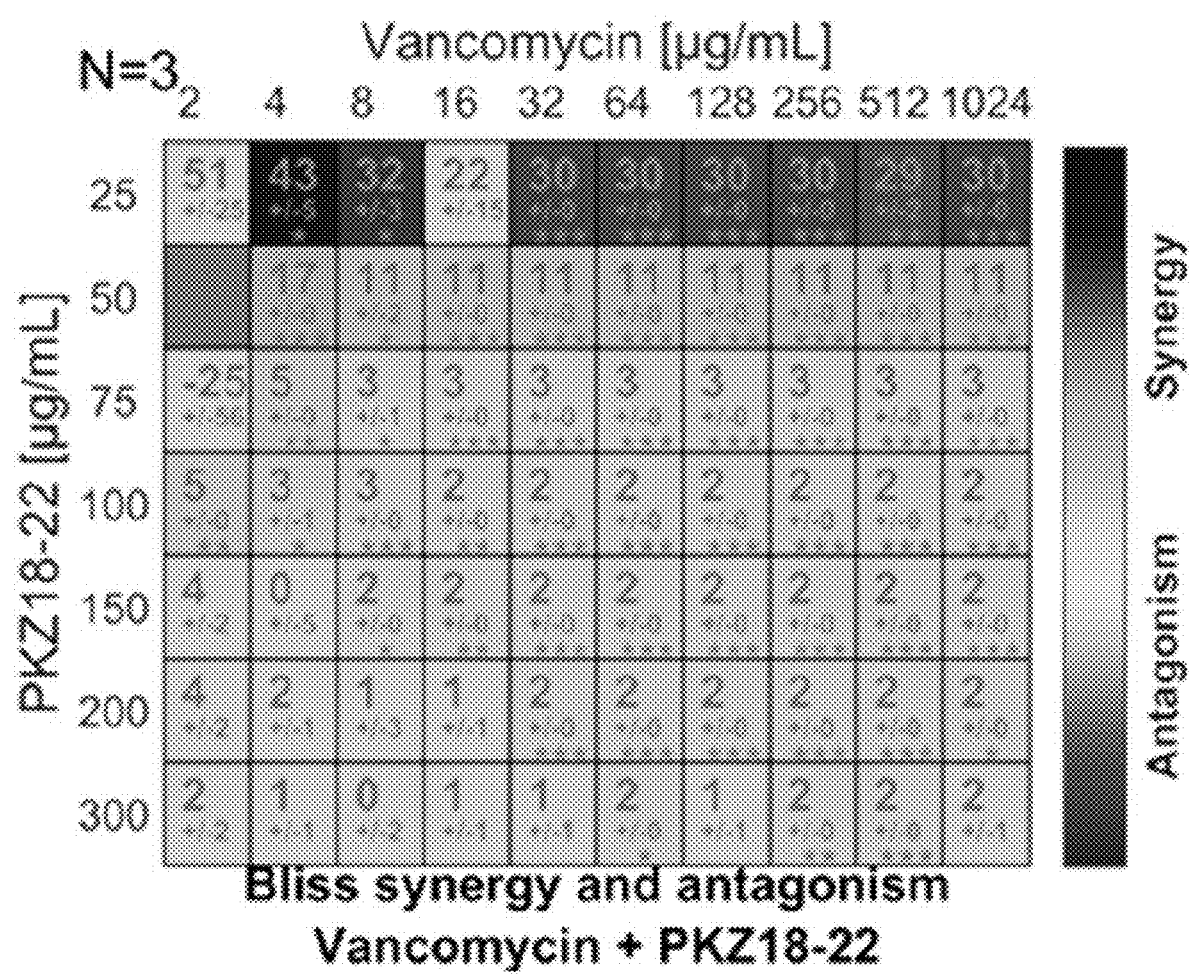

Referring to FIGS. 8, 10, and 11, the Bliss independence model was used to analyze the activity of PKZ18-22 in combination with established antibiotics such as gentamicin, rifampin, and minocycline. The combination of PKZ18-22 (25 µg/mL) and gentamicin (64 µg/mL) demonstrated superior potency against a MRSA (ATCC 29213) biofilm when compared with each using an established MBEC™-HTP biofilm model. Synergistic combinations with a measured score higher than 25 were classified as positive. The highest synergy score of 87 was achieved using a combination of PKZ18-22 (25 µg/mL) and gentamicin (16 µg/mL and 64 µg/mL). These highly synergistic effects were not observed in any of the PKZ18-22 and vancomycin combinations, which reached a maximal synergy score of only 43 (PKZ18-22, 25 µg/mL and vancomycin, 4 µg/mL).

Figure 9:
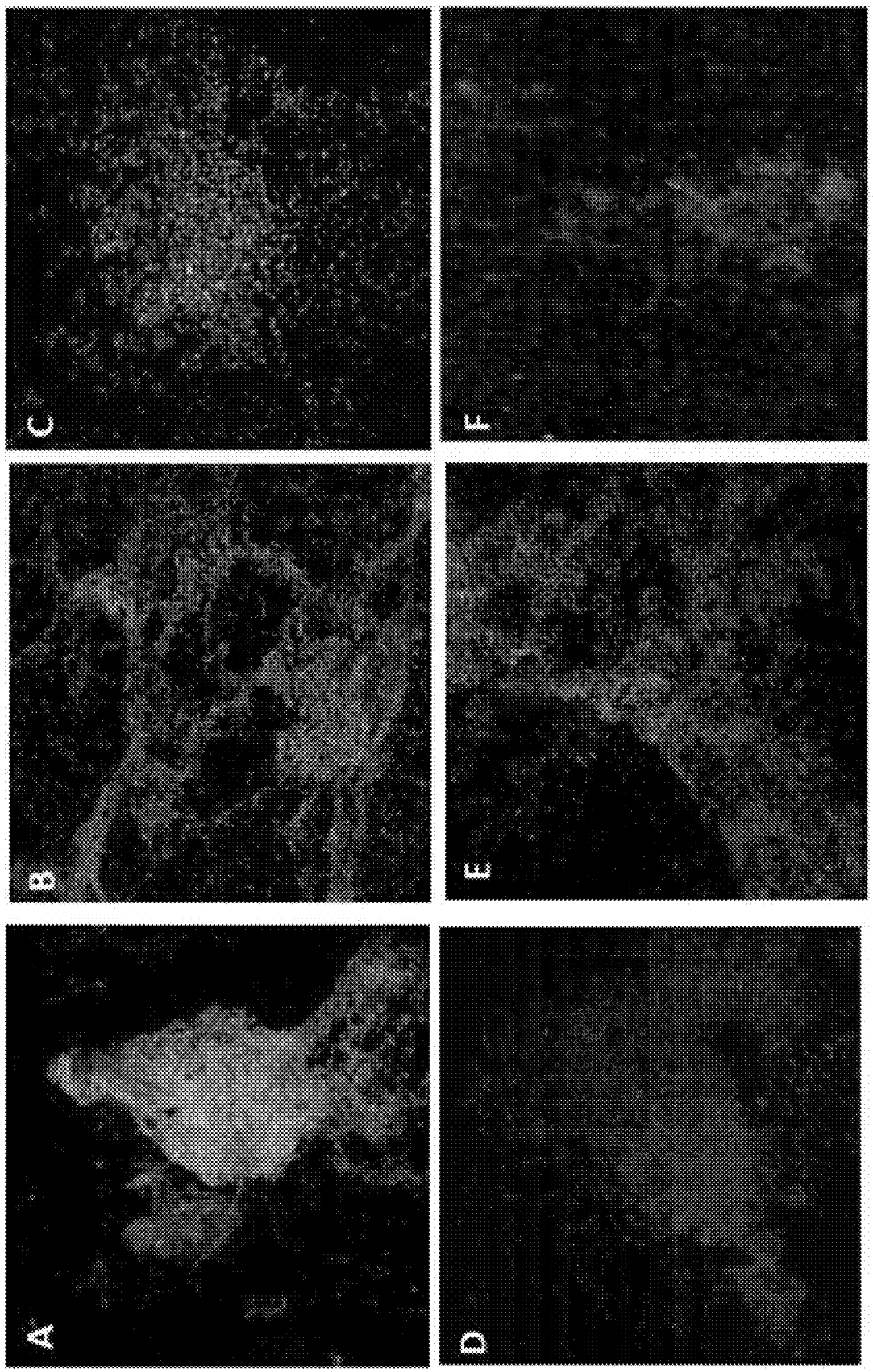
FIG. 9 shows synergistic activity of PKZ18-22 with rifampin. Top left: Biofilm grown for 24 h with no treatment. Top middle: Biofilm growth after 24 h exposure to 25 µg/mL PKZ18-22. Top right: Growth after 24 h exposure to 0.001 µg/mL rifampin. Bottom left: Growth after 24 h exposure to 0.001 µg/mL rifampin+25 µg/mL PKZ18-22. Bottom middle: Growth after 24 h exposure to 0.005 µg/mL rifampin. Bottom right: Growth after 24 h exposure to 0.005 µg/mL rifampin+25 µg/mL PKZ18-22
Figure 12:
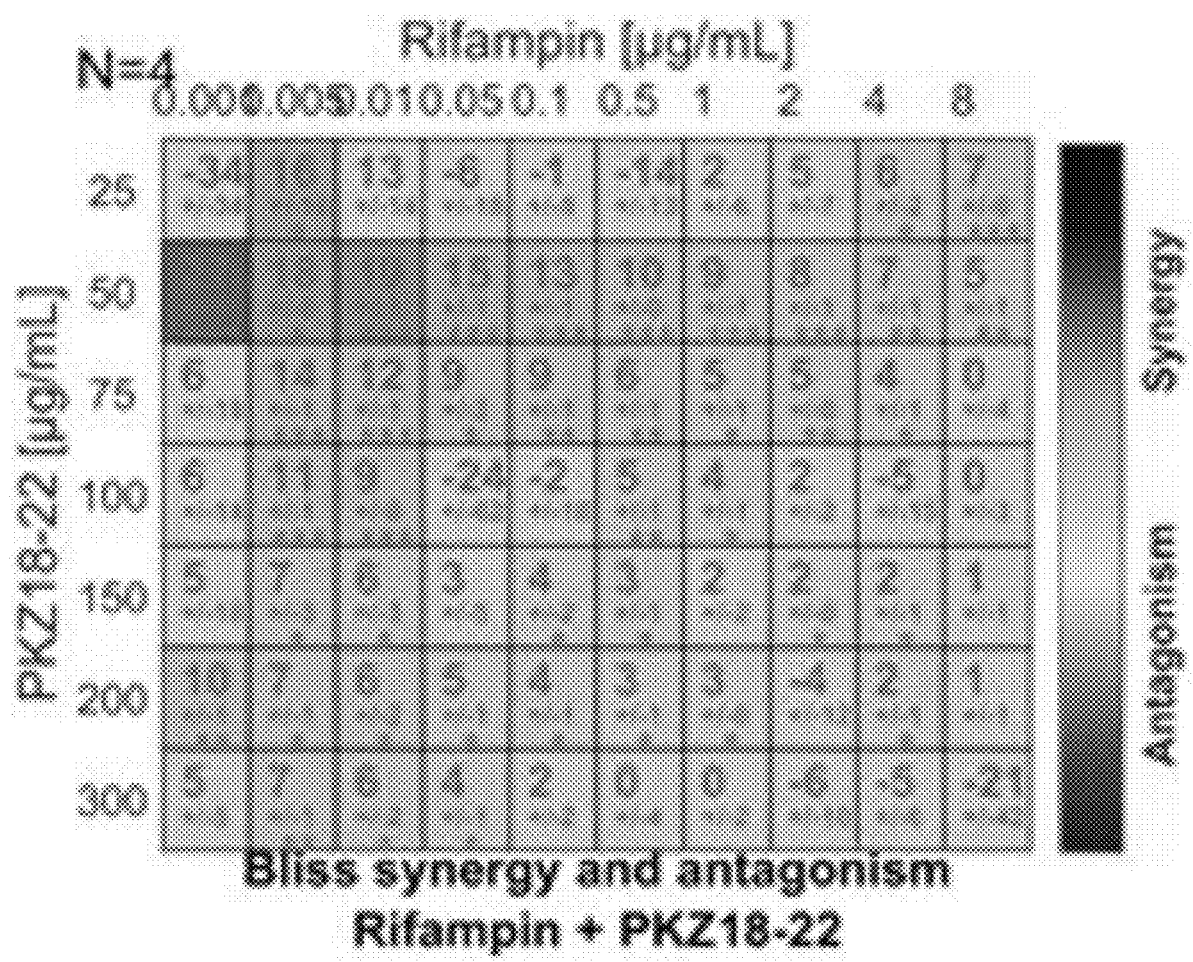
Figure 13A:
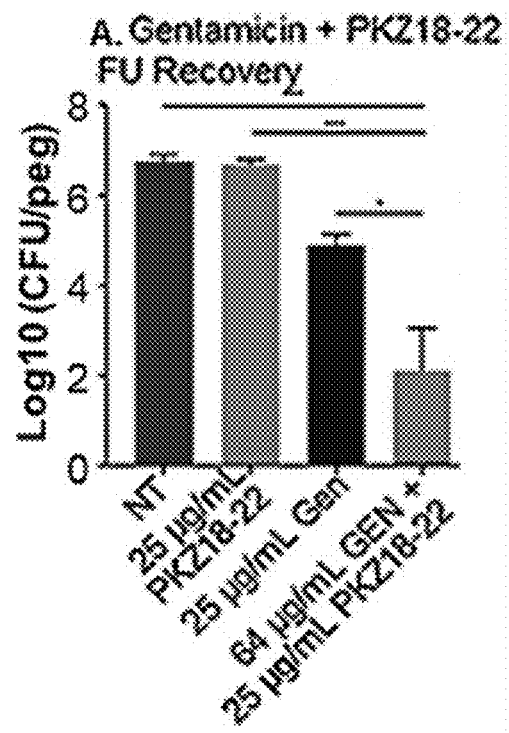
FIGS. 13A-B show PKZ18-22 plus gentamicin inhibition of biofilms in accordance with aspects of the present disclosure.
Figure 13B:
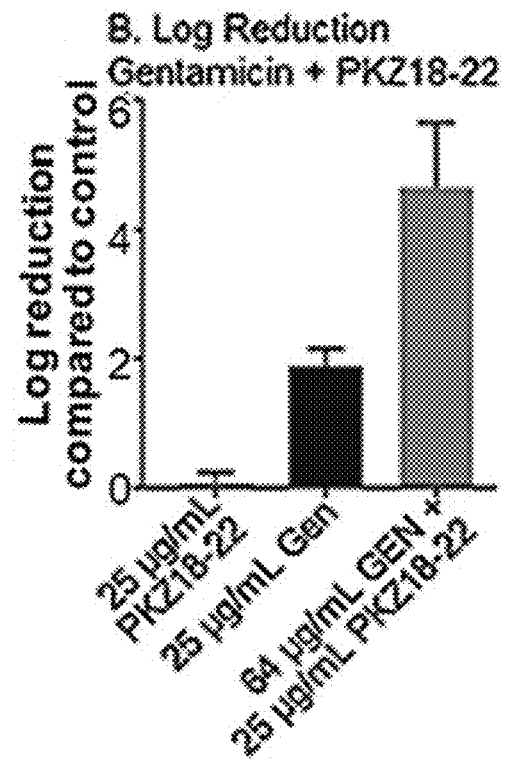
Figure 14:
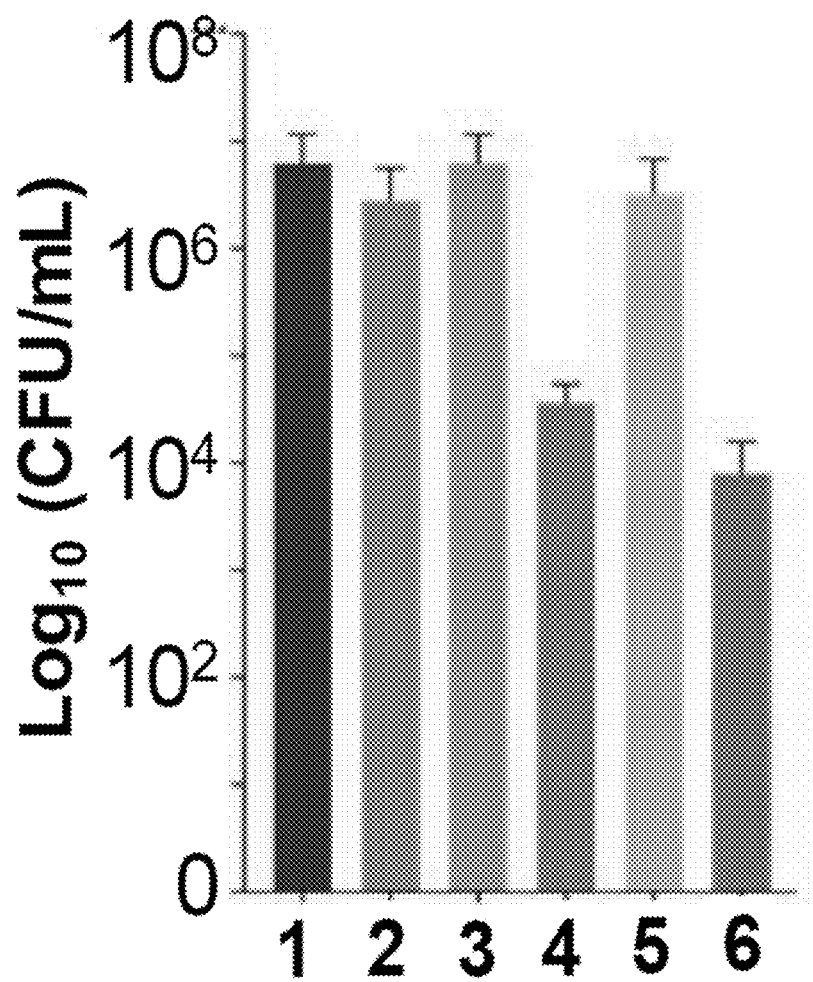
FIG. 14 shows a bar graph of S. aureus biofilm colony forming units following different treatments. 1=S. aureus biofilm colony forming units (CFU/log10) growth not treated; 2=after 24 h of a single dose PKZ18-22 (25 µg/mL); 3=0.001 µg/mL rifampin; 4=0.001 µg/mL rifampin and PKZ18-22 (25 µg/mL); 5=0.005 µg/mL rifampin; 6=0.005 µg/mL rifampin and PKZ18-22 (25 µg/mL). After single dose 24 h challenge, the combination of rifampin and PKZ18-22 produced a significantly greater reduction when compared to each treatment alone.

The most promising combination of PKZ18-22 (25 µg/mL) and gentamicin (64 µg/mL) produced an almost 5 log reduction in CFU/mL in biofilm growth after 24 h exposure (FIGS. 13A-13B). Similar results noted with PKZ18-22 and rifampin (FIGS. 9, 12, and 14). PKZ18-22 concentrations at 25 and 50 µg/mL showed the highest synergy. These highly synergistic effects were not observed in any of the PKZ18-22 and vancomycin combinations. The highest synergy with vancomycin and PKZ18-22, with a score of 43, was noted with a combination of PKZ18-22 (25 µg/mL) and vancomycin (4 µg/mL). When focusing on the most promising combination of PKZ18-22 (25 µg/mL) and gentamicin (64 µg/mL), there was an almost ~5 log reduction after 24 h exposure. The combination of PKZ18-22 with gentamicin exhibited a greater clinical potential to treat methicillin-susceptible *S. aureus* biofilms when compared to any of the PKZ18-22 and vancomycin tested concentrations. After a single dose 24 h challenge, the combination of minocycline and PKZ18-22 did not produce a significantly greater reduction when compared to each treatment alone. Thus, PKZ18-22 was not synergistic with minocycline.

Discussion

Combinatorial usage of compounds of Formula I with aminoglycosides significantly as disclosed herein reduced the concentrations of both drugs needed to inhibit bacterial growth. Aminoglycosides can have drastic side effects, including nephrotoxicity and ototoxicity that leads to permanent damage to the inner ear. Combining aminoglycoside use with use of a compound of Formula I as disclosed herein advantageously enhances a therapeutic effectiveness of aminoglycosides at less toxic levels.

Compounds of Formula I as disclosed herein alone or as a topical formulation or other combination with an aminoglycoside may be a potent therapy for skin infections caused by Gram-positive bacteria such as MRSA. Drugs that can be toxic systemically or do not meet the Lipinski rule of five are commonly used as topical treatments. For example, mupirocin is used as a 2% (0.4 M) solution to treat skin infections, and the formulation for neomycin is 0.5% by mass (3 mM). Activity of compounds of Formula I in nutrient-limited conditions may provide an additional benefit for treatment. Antibiotics need to be functional in nutrient-limited growth environments such as the skin, where the body attempts to gain nutritional immunity and nutrient depletion for pathogens during infection. Synergy of compounds of Formula I as disclosed herein with some aminoglycosides may be especially useful in this context. Aminoglycosides were less effective in nutrient-limited environments than in rich media.

Synergy between compounds of Formula I and other antibiotics such as, without limitation, aminoglycosides as disclosed herein is surprising and advantageous. As disclosed herein, MRSA developed resistance against a compound of Formula I at a surprisingly low frequency compared to most clinically used antibiotics. As disclosed herein, compounds of Formula I provide a promising avenue of targeting Gram-positive pathogens, as they are refractory to resistance, have multiple cellular targets, and can be used in combination with aminoglycoside antibiotics As disclosed herein, biofilm growth is susceptible to a compound of Formula I. Compounds of Formula I are capable of penetrating, in effective concentrations, the EPM. As disclosed herein a compound of Formula I is found to be effective against biofilms and thwarts drug resistance. Surprisingly and advantageously, a compound of Formula I as disclosed herein inhibits biofilm growth synergistically with other antibiotics.

Included in the present disclosure are the following, non-limiting examples of embodiments:

Embodiment 1. A method for inhibiting the growth of Gram-positive bacteria, including contacting said bacteria with a first compound and a second compound, wherein the first compound is a compound of Formula I:

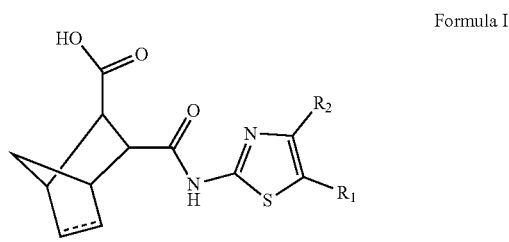

Formula I or a pharmaceutically acceptable salt thereof, wherein

⋯ represents a single or double bond, $R_1$ is selected from hydrogen and $C_{1-3}$ alkyl, $R_2$ is selected from hydrogen, $C_{1-3}$ alkyl, a 5-membered aryl or heteroaryl ring or 6-membered heteroaryl ring wherein said 5-membered aryl or heteroaryl ring or 6-membered heteroaryl ring is optionally substituted with 1, 2, or 3 substituents individually selected from $C_{1-6}$ alkyl and halogen, and a 6-membered aryl ring optionally substituted only with a single $C_{1-6}$ alkyl substituent, the second compound is selected from one or more of an aminoglycoside, a rifamycin, and a glycopeptide antibiotic.

Embodiment 2. The method of embodiment 1, wherein ⋯ represents a single bond.

Embodiment 3. The method of embodiment 1, wherein ⋯ represents a double bond.

Embodiment 4. The method of any one of embodiments 1 through 3, wherein $R_1$ is hydrogen.

Embodiment 5. The method of any one of embodiments 1 through 3, wherein $R_1$ is $C_{1-3}$ alkyl.

Embodiment 6. The method of any one of embodiments 1 through 5, wherein $R_2$ is a 6-membered heteroaryl ring optionally substituted with 1, 2, or 3 substituents individually selected from $C_{1-6}$ alkyl and halogen.

Embodiment 7. The method of any one of embodiments 1 through 6, wherein $R_2$ is a 6-membered heteroaryl ring substituted only with a single $C_{1-6}$ alkyl substituent.

Embodiment 8. The method of any one of embodiments 1 through 7, wherein the compound of Formula I is selected from

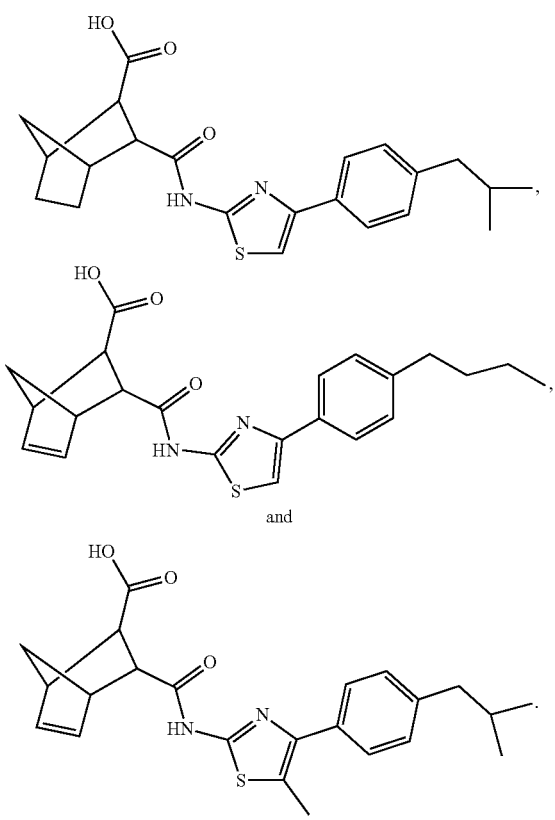

Embodiment 9. The method of any one of embodiments 1 through 8, wherein the second compound is an aminoglycoside.

Embodiment 10. The method of embodiment 9, wherein the aminoglycoside is selected from gentamycin, kanamycin, and neomycin.

Embodiment 11. The method of any one of embodiments 1 through 8, wherein the second compound is a rifamycin.

Embodiment 12. The method of embodiment 11, wherein the rifamycin is rifampin.

Embodiment 13. The method of any one of embodiments 1 through 8, wherein the second compound is a glycopeptide antibiotic.

Embodiment 14. The method of embodiment 13, wherein the glycopeptide antibiotic is vancomycin.

Embodiment 15. The method of any one of embodiments 1 through 14, wherein inhibiting the growth of Gram-positive bacteria includes inhibiting biofilm formation.

Embodiment 16. The method of any one of embodiments 9 through 14 wherein inhibiting the growth of Gram-positive bacteria includes inhibiting biofilm formation.

Embodiment 17. The method of embodiment 8, wherein the second compound is an aminoglycoside.

Embodiment 18. The method of embodiment 8, wherein the second compound is selected from gentamycin, kanamycin, and neomycin.

Embodiment 19. The method of any one of embodiments 1 through 18, wherein contacting said bacteria with a first compound and a second compound includes applying said first compound and said second compound to a surface.

Embodiment 20. The method of embodiment 19, wherein applying includes applying a composition and the composition includes the first compound and the second compound.

Embodiment 21. The method of embodiment 19 or 20, wherein the surface is selected from a skin of a subject, a prosthetic device, a surgical instrument, a table surface, a bench surface, and a cart surface.

Embodiment 22. The method of embodiment 20 or 21, wherein the composition is selected from a cream, an ointment, and a solution.

Embodiment 23. The method of any one of embodiments 1 through 18, wherein contacting said bacteria with said first compound and said second compound includes administering said first compound and said second compound to a subject.

Embodiment 24. The method of embodiment 23, wherein administering includes administering a composition and the composition including said first compound and said second compound.

Embodiment 25. The method of embodiment 23 or 24, wherein administering is administering orally.

Embodiment 26. The method of embodiment 23 or 24, wherein administering is administering intravenously.

Embodiment 27. The method of any one of embodiments 24 through 26, wherein the composition includes a pill, a capsule, or a solution.

Embodiment 28. The method of any one of embodiments 24 through 28, wherein the composition includes a single unit dosage.

Embodiment 29. The composition of any one of embodiments 20, 22, 24, 27, and 28.

Embodiment 30. A pharmaceutical composition, including a first compound and a second compound, wherein the first compound is a compound of Formula I:

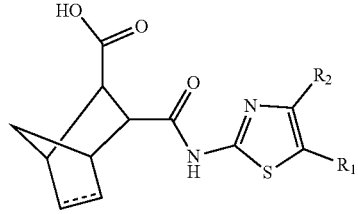

Formula I or a pharmaceutically acceptable salt thereof, wherein
- - - - - represents a single or double bond,
$R_1$ is selected from hydrogen and $C_{1-3}$ alkyl,
$R_2$ is selected from hydrogen, $C_{1-3}$ alkyl, a 5-membered aryl or heteroaryl ring or 6-membered heteroaryl ring wherein said 5-membered aryl or heteroaryl ring or 6-membered heteroaryl ring is optionally substituted with 1, 2, or 3 substituents individually selected from $C_{1-6}$ alkyl and halogen, and a 6-membered aryl ring optionally substituted only with a single $C_{1-6}$ alkyl substituent,
the second compound is selected from one or more of an aminoglycoside, a rifamycin, and a glycopeptide antibiotic.

Embodiment 31. The pharmaceutical composition of embodiment 30, wherein - - - - - represents a single bond.

Embodiment 32. The pharmaceutical composition of embodiment 30, wherein - - - - - represents a double bond.

Embodiment 33. The pharmaceutical composition of any one of embodiments 30 through 32, wherein $R_1$ is hydrogen.

Embodiment 34. The pharmaceutical composition of any one of embodiments 30 through 32, wherein $R_1$ is $C_{1-3}$ alkyl.

Embodiment 35. The pharmaceutical composition of any one of embodiments 30 through 34, wherein $R_2$ is a 6-membered heteroaryl ring optionally substituted with 1, 2, or 3 substituents individually selected from $C_{1-6}$ alkyl and halogen.

Embodiment 36. The pharmaceutical composition of any one of embodiments 30 through 35, wherein $R_2$ is a 6-membered heteroaryl ring substituted only with a single $C_{1-6}$ alkyl substituent.

Embodiment 37. The pharmaceutical composition of any one of embodiments 30 through 36, wherein the compound of Formula I is selected from

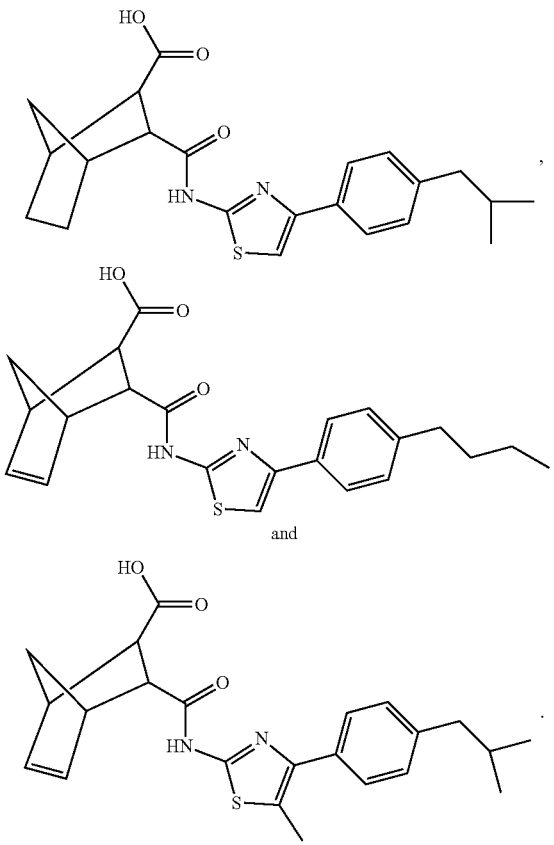

Embodiment 38. The pharmaceutical composition of any one of embodiments 30 through 37, wherein the second compound is an aminoglycoside.

Embodiment 39. The pharmaceutical composition of embodiment 38, wherein the aminoglycoside is selected from gentamycin, kanamycin, and neomycin.

Embodiment 40. The pharmaceutical composition of any one of embodiments 30 through 37, wherein the second compound is a rifamycin.

Embodiment 41. The pharmaceutical composition of embodiment 40, wherein the rifamycin is rifampin.

Embodiment 42. The pharmaceutical composition of any one of embodiments 30 through 37, wherein the second compound is a glycopeptide antibiotic.

Embodiment 43. The pharmaceutical composition of embodiment 42, wherein the glycopeptide antibiotic is vancomycin.

Embodiment 44. The pharmaceutical composition of any one of embodiments 30 through 43, wherein the composition is selected from a cream, an ointment, and a solution.

Embodiment 45. The pharmaceutical composition of any one of embodiments 30 through 44, wherein the composition includes a pill, a capsule, or a solution.

Embodiment 46. The pharmaceutical composition of any one of embodiments 30 through 45, wherein the composition includes a single unit dosage.

What is claimed is:

1. A method for inhibiting the growth of Gram-positive bacteria, comprising contacting said bacteria with a first compound and a second compound, wherein the first compound is a compound of Formula I:

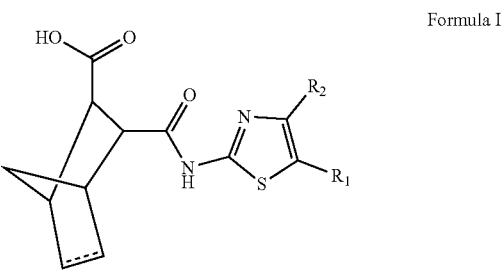

Formula I or a pharmaceutically acceptable salt thereof, wherein
⁃⁃⁃⁃⁃ represents a single or double bond,
$R_1$ is selected from hydrogen and $C_{1-3}$ alkyl,
$R_2$ is selected from hydrogen, $C_{1-3}$ alkyl, a 5-membered aryl or heteroaryl ring or 6-membered heteroaryl ring wherein said 5-membered aryl or heteroaryl ring or 6-membered heteroaryl ring is optionally substituted with 1, 2, or 3 substituents individually selected from $C_{1-6}$ alkyl and halogen, and a 6-membered aryl ring optionally substituted only with a single $C_{1-6}$ alkyl substituent,
the second compound is selected from one or more of an aminoglycoside, a rifamycin, and a glycopeptide antibiotic.

2. The method of claim 1, wherein ⁃⁃⁃⁃⁃ represents a single bond.

3. The method of claim 1, wherein ⁃⁃⁃⁃⁃ represents a double bond.

4. The method of claims 1, wherein $R_1$ is hydrogen.

5. The method of claim 1, wherein $R_1$ is $C_{1-3}$ alkyl.

6. The method of claim 1, wherein $R_2$ is a 6-membered heteroaryl ring optionally substituted with 1, 2, or 3 substituents individually selected from $C_{1-6}$ alkyl and halogen.

7. The method of claim 1, wherein $R_2$ is a 6-membered heteroaryl ring substituted only with a single $C_{1-6}$ alkyl substituent.

8. The method of claim 1, wherein the compound of Formula I is selected from

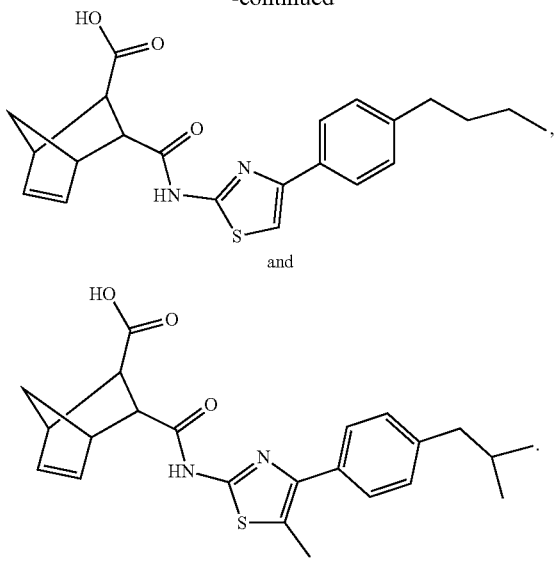

9. The method of claim 1, wherein the second compound is an aminoglycoside.

10. The method of claim 9, wherein the aminoglycoside is selected from gentamycin, kanamycin, and neomycin.

11. The method of claim 1, wherein the second compound is a rifamycin.

12. The method of claim 11, wherein the rifamycin is rifampin.

13. The method of claim 1, wherein the second compound is a glycopeptide antibiotic.

14. The method of claim 13, wherein the glycopeptide antibiotic is vancomycin.

15. The method of claim 1, wherein inhibiting the growth of Gram-positive bacteria comprises inhibiting biofilm formation.

16. The method of claim 9, wherein inhibiting the growth of Gram-positive bacteria comprises inhibiting biofilm formation.

17. The method of claim 8, wherein the second compound is an aminoglycoside.

18. The method of claim 8, wherein the second compound is selected from gentamycin, kanamycin, and neomycin.

19. The method of claim 1, wherein contacting said bacteria with a first compound and a second compound comprises applying said first compound and said second compound to a surface.

20. The method of claim 19, wherein applying comprises applying a composition and the composition comprises the first compound and the second compound.

21. The method of claim 19, wherein the surface is selected from a skin of a subject, a prosthetic device, a surgical instrument, a table surface, a bench surface, and a cart surface.

22. The method of claim 20, wherein the composition is selected from a cream, an ointment, and a solution.

23. A pharmaceutical composition, comprising
a first compound and a second compound, wherein
the first compound is a compound of Formula I:

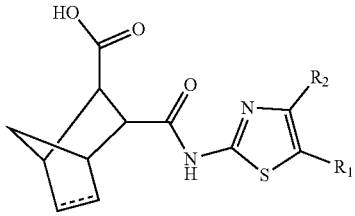

Formula I or a pharmaceutically acceptable salt thereof, wherein
----- represents a single or double bond,
$R_1$ is selected from hydrogen and $C_{1-3}$ alkyl,
$R_2$ is selected from hydrogen, $C_{1-3}$ alkyl, a 5-membered aryl or heteroaryl ring or 6-membered heteroaryl ring wherein said 5-membered aryl or heteroaryl ring or 6-membered heteroaryl ring is optionally substituted with 1, 2, or 3 substituents individually selected from $C_{1-6}$ alkyl and halogen, and a 6-membered aryl ring optionally substituted only with a single $C_{1-6}$ alkyl substituent,
the second compound is selected from one or more of an aminoglycoside, a rifamycin, and a glycopeptide antibiotic.

* * * * *